United States Patent
Abramovitch et al.

(10) Patent No.: US 10,653,679 B2
(45) Date of Patent: May 19, 2020

(54) COMPOSITIONS AND METHODS FOR INHIBITING BACTERIAL GROWTH

(71) Applicant: Board of Trustees of Michigan State University, East Lansing, MI (US)

(72) Inventors: Robert Abramovitch, East Lansing, MI (US); Benjamin K. Johnson, Lansing, MI (US); Christopher J. Colvin, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 15/572,121

(22) PCT Filed: May 4, 2016

(86) PCT No.: PCT/US2016/030689
§ 371 (c)(1),
(2) Date: Nov. 6, 2017

(87) PCT Pub. No.: WO2016/179231
PCT Pub. Date: Nov. 10, 2016

(65) Prior Publication Data
US 2018/0085355 A1    Mar. 29, 2018

Related U.S. Application Data

(60) Provisional application No. 62/156,733, filed on May 4, 2015.

(51) Int. Cl.
| A61K 31/41 | (2006.01) |
| A61K 31/428 | (2006.01) |
| A61K 45/06 | (2006.01) |

(52) U.S. Cl.
CPC ............ *A61K 31/428* (2013.01); *A61K 45/06* (2013.01); *Y02A 50/471* (2018.01); *Y02A 50/473* (2018.01)

(58) Field of Classification Search
CPC .................................................. A61K 31/428

USPC .......................................................... 514/383
See application file for complete search history.

(56) References Cited

U.S. PATENT DOCUMENTS

| 8,207,187 B2 * | 6/2012 | Beck ................. A61K 31/4439 514/292 |
| 2010/0210602 A1 * | 8/2010 | Zhang .................... A61K 31/00 514/152 |
| 2013/0317070 A1 | 11/2013 | Hoffman et al. |
| 2014/0050776 A1 | 2/2014 | Coller et al. |

FOREIGN PATENT DOCUMENTS

| WO | WO-2013/050426 A1 | 4/2013 |
| WO | WO-2014/044838 A1 | 3/2014 |
| WO | WO-2014/176636 A1 | 11/2014 |

OTHER PUBLICATIONS

Perez et al., Molecular Microbiology, 2001, 41(1): 179-187.*
Capasso et al. publication, Expert Opin, Ther Patents, 2013, 23(6):693-704.*
Carta et al., Bioorg Med Chem Lett, 2009, 19(23):6649-6654.*
International Search Report and Written Opinion for International Application No. PCT/US16/30689 dated Aug. 4, 2016.
Minakuchi et al., "Molecular Cloning, Characterization, and Inhibition Studies of the Rv1284 Beta-Carbonic Anhydrase from *Mycobacterium tuberculosis* with Sulfonamides and a Sulfamate," Journal of Medicinal Chemistry, 52: 2226-2232 (2009).

* cited by examiner

*Primary Examiner* — Rei Tsang Shiao
(74) *Attorney, Agent, or Firm* — Foley Hoag LLP

(57) ABSTRACT

The present disclosure provides, among other things, compositions and methods useful for inhibiting bacteria, such as *Mycobacterium tuberculosis*. These compositions and methods find many uses in medicine and research, e.g., treating subjects afflicted with active or latent bacterial infections. The compositions described herein are also useful for decontaminating surfaces (e.g., surgical tools or implants).

22 Claims, 18 Drawing Sheets

Specification includes a Sequence Listing.

__US 10,653,679 B2__

COMPOSITIONS AND METHODS FOR INHIBITING BACTERIAL GROWTH

CROSS REFERENCE TO RELATED APPLICATIONS

This application is a national stage filing under 35 U.S.C. § 371 of PCT/US16/030689, filed on May 4, 2016, which claims the benefit of U.S. Provisional Application No. 62/156,733, filed May 4, 2015, the contents of each of which are specifically incorporated herein by reference in their entirety.

STATEMENT OF GOVERNMENT SUPPORT

This invention was made with government support under AI105867 and AI057153 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 6, 2019, is named MSS-01201_SL.txt and is 10,236 bytes in size.

BACKGROUND

*Mycobacterium tuberculosis* (Mtb) causes tuberculosis (TB) and is responsible for nearly two million deaths annually. In addition, a substantial proportion of the millions of people living with HIV/AIDS worldwide are co-infected with Mtb. And recently, multi-drug resistant (MDR) tuberculosis as well as extensively drug-resistant (XDR) tuberculosis have evolved, which further restricts treatment options for patients and threatens TB control and prevention efforts. Thus, there is a need in the art for new, effective treatments for TB.

SUMMARY

The disclosure is based, at least in part, on the discovery that the carbonic anhydrase antagonist, ethoxzolamide (ETZ), inhibits the PhoP/R regulon in *Mycobacterium tuberculosis*. This pH-dependent regulon controls, among other things, production of cell envelope lipids (such as sulfolipid) and is a virulence factor for the pathogenesis of tuberculosis. ETZ not only inhibits the PhoP/R regulon, but also inhibits growth of tuberculosis bacteria in macrophages in vivo. These observations indicate, among other things, that carbonic anhydrase inhibitors, as well as other compounds that inhibit the PhoP/R regulon, are useful for treating infections by bacteria in which the PhoPR regulon is conserved.

One of skill in the art would appreciate that there are several benefits to the use of the instantly-disclosed inhibitors and methods. For example, current treatment schedules for tuberculosis infection involve a regimen of at least four compounds (isoniazid, rifampicin, ethambutol, and pyrazinamide) coadministered over a prolonged period (e.g., 6-9 months). The instantly disclosed compositions, when used alone or in combination with one or more additional agents (e.g., isoniazid, rifampicin, ethambutol, and pyrazinamide), are believed to effectively treat an infection in a shorter period of time, e.g., less than 8 weeks (e.g., less than 7 weeks, 6 weeks, 5 weeks, 4 weeks, 3 weeks, or 2 weeks) or between 2 to 4 weeks. Thus, the instantly disclosed compositions offer the opportunity for increased patient compliance. The compositions are also useful for treating immunocompromised subjects (e.g., subjects afflicted with an HIV infection) and/or subjects with latent bacterial infections. Moreover, the compositions and methods described herein are useful for treating drug-resistant bacterial infections, such as infections with MDR and/or XDR tuberculosis.

Accordingly, in one aspect, the disclosure features a method for inhibiting growth or viability of one or more bacterial cells in which the PhoPR regulon is present or conserved. The method comprises contacting the one or more bacterial cells with an effective amount of an inhibitor of the PhoP/R regulon (e.g., an inhibitor of PhoP or PhoR) to thereby inhibit the growth or viability of the one or more bacterial cells. The contacting can occur in vitro (e.g., cultured bacteria), in macrophages or other immune cell hosts, or in vivo (e.g., in a human or non-human mammal).

In another aspect, the disclosure features a method for preventing or reducing the likelihood of a productive bacterial infection in a subject. The method comprises administering to a subject an effective amount of an inhibitor of the PhoP/R regulon to thereby prevent or reduce the likelihood of a productive bacterial infection in the subject. The subject can be one identified as being at risk of developing an infection with bacteria cells in which the PhoPR regulon is present or conserved.

In another aspect, the disclosure features a method for treating a subject who is infected with bacterial cells in which the PhoPR regulon is present or conserved, which method comprises administering to the subject an effective amount of an inhibitor of the PhoP/R regulon to thereby treat the infection.

In yet another aspect, the disclosure features a method for ameliorating the signs or symptoms of an infection of a subject by bacterial cells in which the PhoPR regulon is present or conserved. The method comprises administering to the subject an effective amount of an inhibitor of the PhoP/R regulon to thereby ameliorate the signs and symptoms of the infection.

In some embodiments, any of the methods described herein comprise identifying the subject as having an infection with bacterial cells in which the PhoPR regulon is present or conserved. In some embodiments, any of the methods described herein comprise identifying the subject as being at risk of developing an infection with bacterial cells in which the PhoPR regulon is present or conserved.

In some embodiments of any of the methods described herein, the bacteria or bacterial cells are of the genus *Mycobacterium*. In some embodiments, the *Mycobacterium* are *Mycobacterium tuberculosis*. In some embodiments, the *Mycobacterium tuberculosis* is multi-drug resistant *Mycobacterium tuberculosis*. In some embodiments, the *Mycobacterium tuberculosis* is extensively drug resistant *Mycobacterium tuberculosis*.

In some embodiments, the bacteria or bacterial cells are *Clostridium* (e.g., *C. acetobutylicum*) or *Bacillus* (e.g., *B. subtilis*).

One of skill in the art will appreciate that the PhoPR regulon is conserved in many other types of bacteria, such as *Escherichia coli* and *Vibrio cholerae*, in which the PhoPR system is encoded by the PhoBR operon (see, e.g., Diniz et al. (2011) *J. Bacteriol* 193(24):6929-6938), whereas the system is encoded by PhoRP in *Streptomyces coelicolor*. Such bacteria or bacterial cells are also amenable to treatment with the inhibitors described herein. In addition, The homologous pH- and Mg-sensing system PhoPQ exists in a variety of important pathogens belonging to the Enterobacteriaceae, including *Salmonella* spp., *Yersinia pestis*, *Shigella* spp., *E. coli, Pseudomonas* spp. and many others.

In another aspect, the disclosure features a method for eliminating dormant *Mycobacterium tuberculosis* cells in a subject afflicted with latent tuberculosis. The method comprises administering to the subject an effective amount of an inhibitor of PhoR or PhoP to thereby eliminate dormant *Mycobacterium tuberculosis* cells in the subject and treat latent tuberculosis. In some embodiments, the methods comprise determining that the subject has latent tuberculosis. In some embodiments, the *Mycobacterium tuberculosis* is multi-drug resistant *Mycobacterium tuberculosis*. In some embodiments, the *Mycobacterium tuberculosis* is extensively drug resistant *Mycobacterium tuberculosis*.

In some embodiments, the bacteria or bacterial cells are nontuberculous mycobacteria (NTM). The skilled artisan will appreciate that the PhoPR is conserved in many NTMs. The NTM can be, without limitation, *M. avium, M. intracellulare, M. kansasii, M. abscessus, M. chelonae, M. fortuitum, M. terrae, M. xenopi*, or *M. simiae*. In some embodiments, the NTM is *M. leprae, M. ulcerans*, or *M. marinum*.

Many species of NTM cause serious skin and ocular infections. In such embodiments, topical treatment with a compound described herein may be useful treatment as a monotherapy (e.g., as a cream, a salve, an ointment, an eye drop, or even applied to a bandage). Alternatively, one or more compounds described herein may synergize with traditional antibiotics by inhibiting survival in macrophages. NTM skin infections can be recalcitrant to treatment and sometimes very serious such as Buruli ulcer (caused by *Mycobacterium ulcerans*) and *Mycobacterium abscessus*, which causes skin and ear infections in immunocompromised individuals.

In some embodiments of any of the methods described herein, the inhibitor of PhoR or PhoP is a carbonic anhydrase inhibitor. The carbonic anhydrase inhibitor can be, e.g., a sulfonamide. For example, in some embodiments, the sulfonamide is ethoxzolamide (ETZ). In some embodiments, the carbonic anhydrase inhibitor is a ethoxzolamide analog. In some embodiments, the carbonic anhydrase inhibitor is acetazolamide, methazolamide, dorzolamide, or brinzolamide. In some embodiments, the carbonic anhydrase inhibitor is any one of those described herein (e.g., by reference) or those known in the art.

In another aspect, the disclosure features a method for treating tuberculosis in a subject, the method comprising administering to the subject a carbonic anhydrase inhibitor in an amount effective to treat tuberculosis. The carbonic anhydrase inhibitor can be, e.g., ethoxzolamide (ETZ). In some embodiments, the carbonic anhydrase inhibitor is a ethoxzolamide analog. In some embodiments, the carbonic anhydrase inhibitor is acetazolamide, methazolamide, dorzolamide, or brinzolamide. In some embodiments, the carbonic anhydrase inhibitor is any one of those described herein (e.g., by reference) or those known in the art. In some embodiments, the *Mycobacterium tuberculosis* is multi-drug resistant *Mycobacterium tuberculosis*. In some embodiments, the *Mycobacterium tuberculosis* is extensively drug resistant *Mycobacterium tuberculosis*. In some embodiments, the infection is a nosocomial infection.

In some embodiments of any of the methods described herein, the subject is a non-human primate.

In some embodiments of any of the methods described herein, the subject is a cow, a pig, a horse, a goat, a sheep, a bird (e.g., chicken, turkey, quail, or pheasant), or other domesticated livestock animal.

In some embodiments of any of the methods described herein, the subject is a human (e.g., a man or woman of any age: child, infant, toddler, or adult).

In some embodiments, the subject has a respiratory infection, e.g., a lung infection. In some embodiments, the subject has an eye infection. In some embodiments, the subject has an ear infection. In some embodiments, the subject has a gastrointestinal infection (e.g., an infection of the stomach or intestine). In some embodiments, the subject has a urinary tract infection. In some embodiments, the subject has a skin infection (e.g., an ulcer, a decubitus ulcer, or a chronic wound, such as one associated with diabetes, a cardiovascular disorder, or circulatory disorder).

In some embodiments, the subject is immunocompromised. For example, in some embodiments the subject (e.g., a human) has cancer, is being treated with immunosuppressive therapy, and/or is infected with HIV (e.g., a human infected with HIV-1).

In some embodiments of any of the methods described herein, the effective amount of the carbonic anhydrase inhibitor (e.g., ETZ or ETZ analog) is between 0.01 mg and 100 mg per kg body weight of the subject.

In some embodiments of any of the methods described herein, the inhibitor is administered as a short-term treatment, e.g., less than 8 weeks (e.g., less than 7 weeks, 6 weeks, 5 weeks, 4 weeks, 3 weeks, or 2 weeks), between 1 to 5 weeks, between 2 to 4 weeks, between 1 to 3 weeks, or between 2 to 5 weeks.

In some embodiments of any of the methods described herein, the inhibitor is orally administered to the subject. In some embodiments of any of the methods described herein, the inhibitor is parenterally administered to the subject. For example, the inhibitor can be administered intravenously.

In some embodiments, the inhibitor is administered as an aerosol, e.g., using a nebulizer or inhaler.

In some embodiments of any of the methods described herein, the inhibitor is administered with one or more antibiotics, such as isoniazid, rifampicin, ethambutol, and pyrazinamide (e.g., in the treatment of tuberculosis).

In another aspect, the disclosure features an aerosol composition comprising any one or more of the inhibitors described herein, e.g., for use in treating or preventing a bacterial infection, such as an active or latent bacterial infection described herein. The inhibitor is formulated in a composition suitable for aerosolization. The inhibitor may be formulated in combination with an additional active agent, and the combination formulation is suitable for aerosolization. Alternatively, the inhibitor and an additional active agent may be formulated separately, such that they will be combined after aerosolization occurs or after being administered to a subject.

In another aspect, the disclosure features a nebulization composition comprising one or more of any of the inhibitors described herein, e.g., for use in treating or preventing a bacterial infection, such as an active or latent bacterial infection described herein. The inhibitor can be formulated in a composition suitable for nebulization. Similarly, the inhibitor may be formulated in combination with an additional active agent, and the combination formulation is suitable for nebulization. Alternatively, the inhibitor and an additional active agent may be formulated separately, such that they will be combined after nebulization occurs or after being administered to a subject.

In another aspect, the disclosure provides a biopharmaceutical package comprising one or more of any of the inhibitors described herein, e.g., for use in treating or preventing a bacterial infection, such as an active or latent bacterial infection described herein. The biopharmaceutical package may further comprise an active agent in addition to the inhibitor(s). The biopharmaceutical package may also comprise instructions for use.

In yet another aspect, the disclosure provides a composition (e.g., a sterile aqueous or powdered (lyophilized) composition) comprising one or more of any of the inhibitors described herein, e.g., for use in inhibiting bacterial growth. For example, the composition can be a cleaning solution, or additive for a cleaning solution, used to decontaminate surfaces, e.g., surgical tools or tables. In another example, the compositions can be suitable as soaking solutions or perfusion solutions for transplant organs or implants to be transplanted or implanted in a subject.

In another aspect, the disclosure features a pharmaceutical composition for use in topical treatment of an infection with bacterial cells in which the PhoPR regulon is conserved, such as, but not limited to, any one of the nontuberculosis bacteria known in the art or described herein. The pharmaceutical composition can comprise, e.g., one or more carbonic anhydrase inhibitors. The carbonic anhydrase inhibitor can be any of those known in the art or described herein.

In some embodiments, the compositions are formulated as an eye drop. In some embodiments, the compositions are formulated as an ointment, lotion, gel, cream, aerosol, spray, or salve. In some embodiments, the compositions comprise one or more antibiotics for use in treating bacterial infections.

In another aspect, the disclosure features a sterile bandage or dressing for use in treating a wound or other cutaneous infection. The bandage or dressing comprises (or is impregnated with) a carbonic anhydrase inhibitor in an amount effective to inhibit the growth or viability of bacterial cells in which the PhoPR regulon is conserved. The carbonic anhydrase inhibitor can be any of those known in the art or described herein. In some embodiments, the bandage or dressing can be for surgical use and can contact cutaneous surfaces as well as internal surfaces.

In yet another aspect, the disclosure provides a screening method to identify a compound that inhibits the PhoP/R regulon. The method comprises screening a plurality of compounds for activity in a cell (e.g., a bacterial cell) that expresses a pH-inducible reporter gene (e.g., GFP) controlled by the PhoP/R regulon. A reduction in expression of the reporter gene (e.g., a reduction in detectable signal produced from the protein product of the gene) in the presence of the a candidate compound, as compared to the level of signal in the absence of the compound, indicates that a compound inhibits the PhoP/R operon. Such a screening method is exemplified in the working examples.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for treating bacterial infections, will be apparent from the following description, the examples, the drawings, and from the claims.

DETAILED DESCRIPTION

Figure 1:
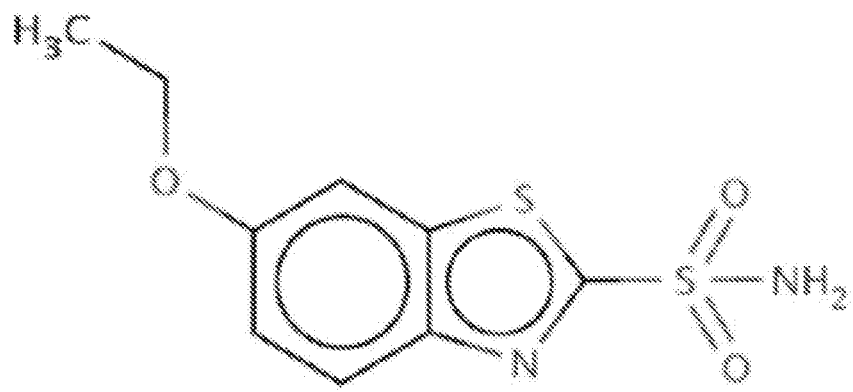
FIG. 1 includes four panels, A-D, and depicts ethoxzolamide (ETZ) inhibition of PhoPR-regulated aprA'::GFP fluorescence and Mtb carbonic anhydrase activity. (Panel A) Chemical structure of ethoxzolamide (ETZ) [6-ethoxy-1,3-benzothiazole-2-sulfonamide]. (Panel B) ETZ inhibits PhoPR-dependent CDC1551(aprA'::GFP) fluorescence in a concentration dependent manner at pH 5.7 with an EC50 of 5.6 µM and little effect on growth. (Panel C) Mtb carbonic anhydrase activity is not detectable in whole cells when treated with ETZ (80 µM) compared to a DMSO control. (Panel D) Mtb treated with ETZ (80 µM) for 6 days exhibits no change of cytoplasmic pH at pH 7.0 and only slightly acidified cytoplasm (<0.1 pH units) at pH 5.7. Data are representative of at least two biological replicates, error bars are the standard deviation of at least three technical replicates, * p<0.05 calculated based on a two-tailed t-test.
Figure 1:
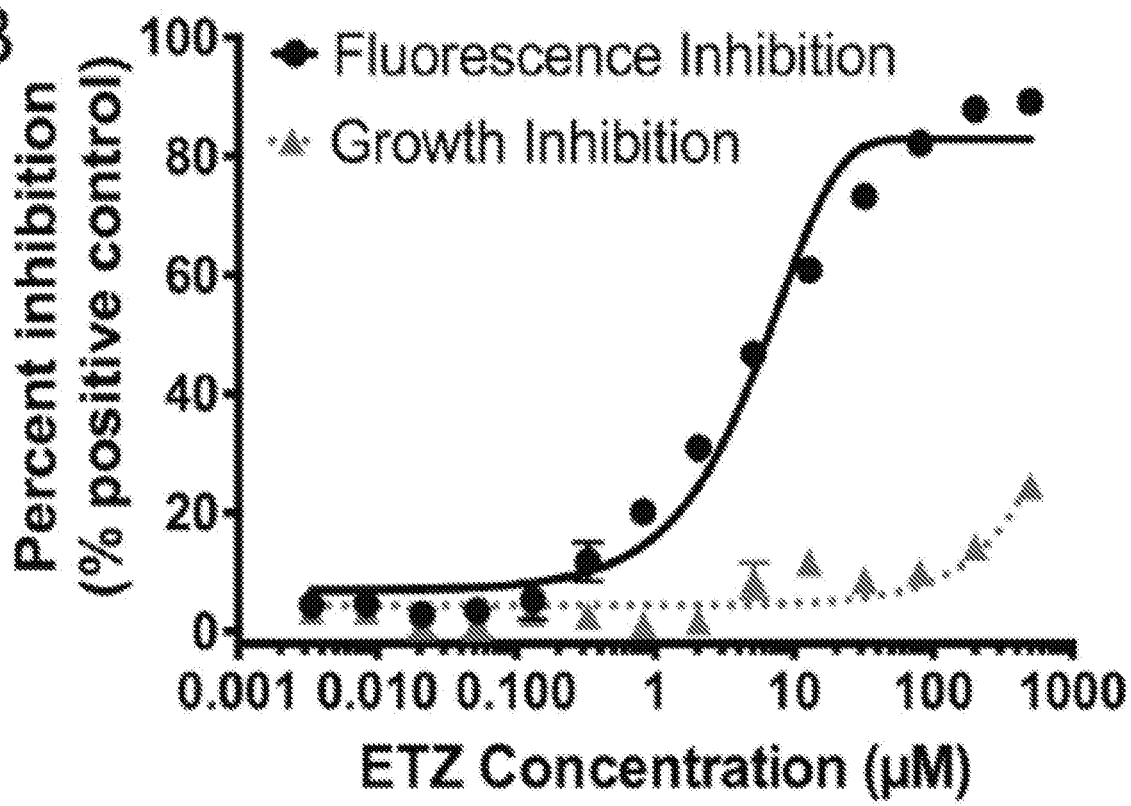
Figure 1:
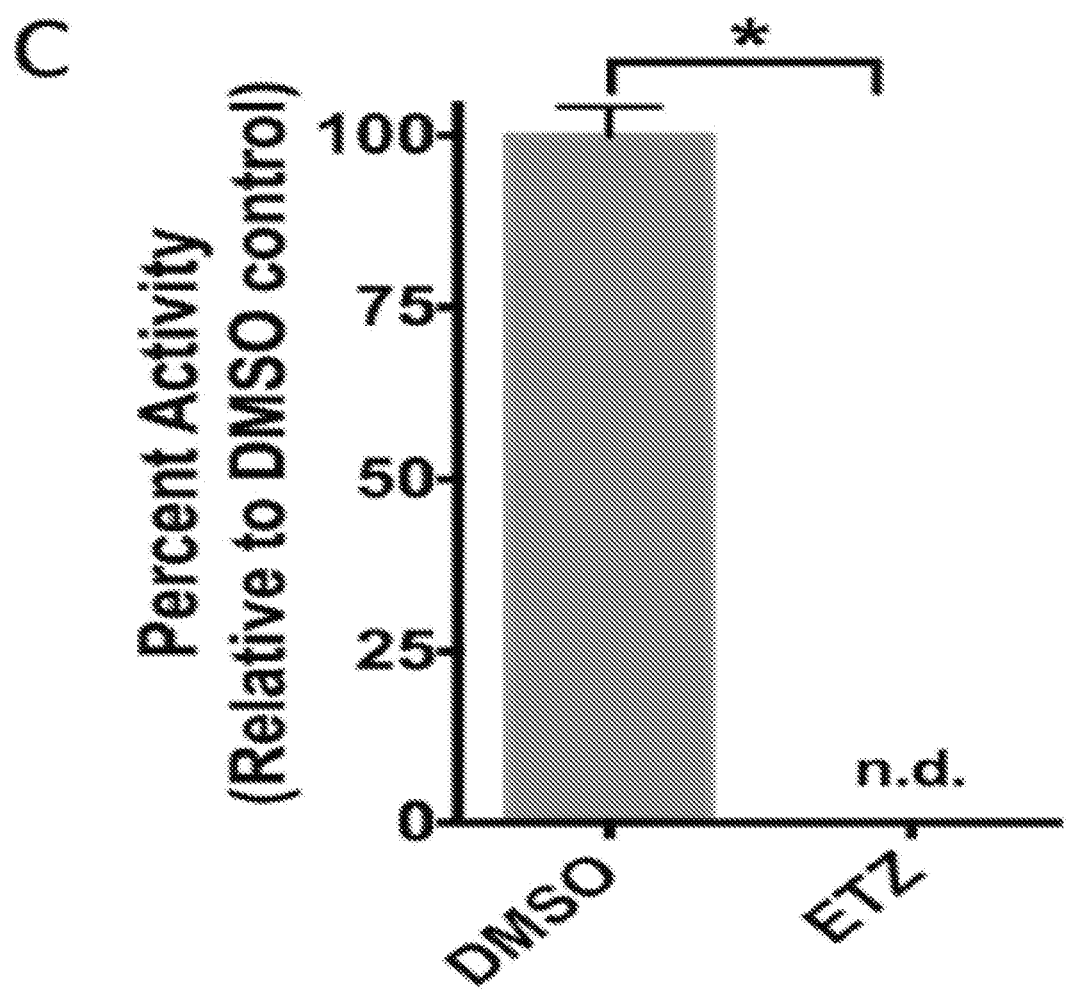
Figure 1:
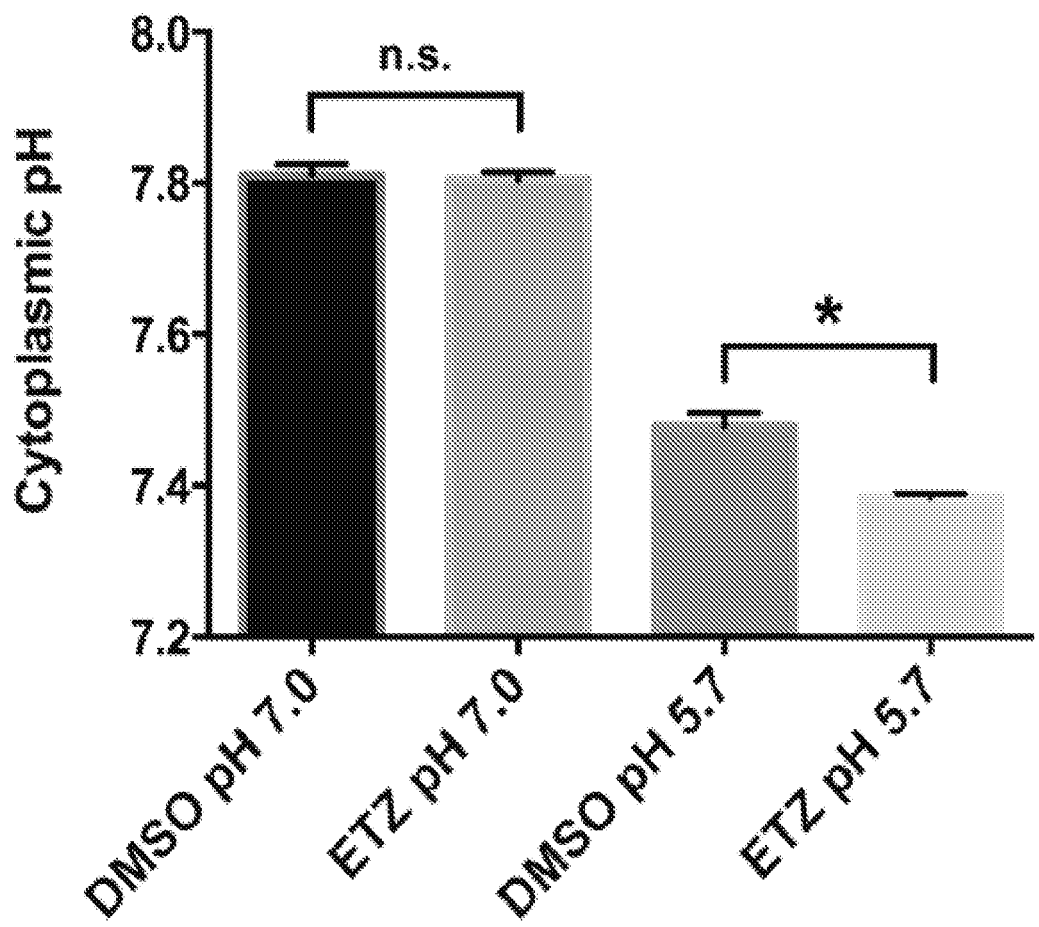

The present disclosure provides, among other things, compositions and methods useful for inhibiting bacteria, such as *Mycobacterium tuberculosis*. These compositions and methods find many uses in medicine and research, e.g., treating subjects afflicted with active or latent bacterial infections. While in no way intended to be limiting, exemplary compositions and methods are elaborated on below.

Inhibitors of the PhoPR Regulon

The disclosure features, among other things, in vitro and in vivo methods for inhibiting the growth or viability of bacteria, such as *Mycobacterium tuberculosis*, using inhibitors of the PhoPR regulon. As used herein, "inhibition of the PhoPR regulon" or similar grammatical terms and phrases, includes direct and indirect inhibition of the regulon. For example, an inhibitor of the PhoPR regulon can be one that directly binds to PhoP protein or PhoR protein and inhibits the activity of the protein. In some embodiments, the inhibitor can be one that inhibits the expression or stability of PhoP or PhoR protein. In some embodiments, the inhibitor inhibits a protein regulator of the PhoPR regulon.

In some embodiments, the inhibitor can inhibit the ability of PhoP to bind to DNA (see, e.g., He and Wang (2014) *Biochemistry* 53(51):8008-8020 and Gupta et al. (2009) J Bacteriol 191(24):7466-7476, which describe DNA binding motifs for *Mycobacterium tuberculosis* PhoP). In some embodiments, the inhibitor inhibits the ability of PhoP to enhance or repress the expression of a target gene, such as any of those described in the tables provided herein. In some embodiments, an inhibitor can inhibit the kinase activity of PhoR. Methods for measuring DNA binding activity and kinase activity are well known in the art.

As used herein, the term "inhibiting" and grammatical equivalents thereof refer to a decrease, limiting, and/or blocking of a particular action, function, or interaction. In one embodiment, the term refers to reducing the level of a given output or parameter to a quantity which is at least 10%, 15%, 20%, 25%, 30%, 35%, 40%, 45%, 50%, 55%, 60%, 65%, 70%, 75%, 80%, 85%, 90%, 95%, 99% or less than the quantity in a corresponding control. A reduced level of a given output or parameter need not, although it may, mean an absolute absence of the output or parameter. The disclosure does not require, and is not limited to, methods that wholly eliminate the output or parameter.

The inhibitor can be, e.g., a small molecule, a protein, a protein fragment, a polypeptide, a peptide, a polypeptide analog, a peptidomimetic, a nucleic acid, a nucleic acid analog, a macrocyle compound, an aptamer including but not limited to an RNA aptamer including an L-RNA aptamer, a spiegelmer, a locked nucleic acid (LNA), a peptide nucleic acid (PNA), or an antibody.

In some embodiments of any of the methods described herein, the inhibitor of the PhoPR regulon is a carbonic anhydrase inhibitor. The carbonic anhydrase inhibitor can be, e.g., a sulfonamide. For example, in some embodiments, the sulfonamide is ethoxzolamide (ETZ). In some embodiments, the sulfonamide is a ethoxzolamide analog. In some embodiments, the sulfonamide is acetazolamide, methazolamide, dorzolamide, or brinzolamide (see, e.g., U.S. Pat. No. 4,221,783). In some embodiments, the carbonic anhydrase inhibitor is any one of those described herein (e.g., by reference) or those known in the art. In some embodiments, the carbonic anhydrase inhibitor is one identified in U.S. Patent Application Publication No. 20130053392 and 20030100594; International Patent Application Publication No. WO 1997/030704; and U.S. Pat. Nos. 5,095,026 and 4,629,738, the disclosures of each of the foregoing (as they relate to such compounds) is incorporated herein by reference in their entirety.

Methods for determining whether a compound has carbonic anhydrase activity are known in the art and described in, e.g., U.S. Patent Application Publication No. 20130053392 and 20030100594; International Patent Application Publication No. WO 1997/030704; and U.S. Pat. Nos. 5,095,026 and 4,629,738. Methods for identifying or designing additional useful carbonic anhydrase inhibitors are known in the art and described in, e.g., Ivanova et al. (2015) "X-ray crystallography-promoted drug design of carbonic anhydrase inhibitors" *Chem Commun (Carob)* 51(33):7108-7111, the disclosure of which is incorporated herein by reference in its entirety.

For use in the identification of additional carbonic anhydrase inhibitors, skilled artisans would be well aware of the amino acid sequences of bacterial carbonic anhydrase enzymes, such as those from *Mycobacterium tuberculosis*. For example, *Mycobacterium tuberculosis* has three carbonic anhydrase genes (Rv3273, Rv1284, and Rv3588c), of which the latter two are required for survival of *Mycobacterium tuberculosis* in mice.

An exemplary amino acid sequence for Rv3273 of *Mycobacterium tuberculosis* is as follows:

MTIPRSQHMSTAVNSCTEAPASRSQWMLANLRHDVPASLVVFLVALPLSL

GIAIASGAPIIAGVIAAVVGGIVAGAVGGSPVQVSGPAAGLTVVVAELID

ELGWPMLCLMTIAAGALQIVFGLSRMARAALAIAPVVVHAMLAGIGITIA

LQQIHVLLGGTSHSSAWRNIVALPDGILHHELHEVIVGGTVIAILLMWSK

LPAKVRIIPGPLVAIAGATVLALLPVLQTERIDLQGNFFDAIGLPKLAEM

SPGGQPWSHEISAIALGVLTIALIASVESLLSAVGVDKLHHGPRTDFNRE

MVGQGSANVVSGLLGGLPITGVIVRSSANVAAGARTRMSTILHGVWILLF

ASLFTNLVELIPKAALAGLLIVIGAQLVKLAHIKLAWRTGNFVIYAITIV

CVVFLNLLEGVAIGLVVAIVFLLVRVVRAPVEVKPVGGEQSKRWRVDIDG

TLSFLLLPRLTTVLSKLPEGSEVTLNLNADYIDDSVSEAISDWRRAHETR

GGVVAIVETSPAKLHHAHARPPKRHFASDPIGLVPWRSARGKDRGSASVL

DRIDEYHRNGAAVLHPHIAGLTDSQDPYELFLTCADSRILPNVITASGPG

DLYTVRNLGNLVPTDPDDRSVDAALDFAVNQLGVSSVVVCGHSSCAAMTA

LLEDDPANTTTPMMRWLENAHDSLVVFRNHHPARRSAESAGYPEADQLSI

-continued

VNVAVQVERLTRHPILATAVAAADLQVIGIFFDISTARVYEVGPNGIICP

DEPADRPVDHESAQ (SEQ ID NO:1, Uniprot Id. No. P96878). An exemplary amino acid sequence for Rv1284 of *Mycobacterium tuberculosis* is as follows:

MTVTDDYLANNVDYASGFKGPLPMPPSKHIAIVACMDARLDVYRMLGIKE

GEAHVIRNAGCVVTDDVIRSLAISQRLLGTREIILLHHTDCGMLTFTDDD

FKRAIQDETGIRPTWSPESYPDAVEDVRQSLRRIEVNPFVTKHTSLRGFV

FDVATGKLNEVTP (SEQ ID NO:2, Uniprot Id. No. P9WPJ7). And an exemplary amino acid sequence for Rv3588c of *Mycobacterium tuberculosis* is as follows:

MPNTNPVAAWKALKEGNERFVAGRPQHPSQSVDHRAGLAAGQKPTAVIFG

CADSRVAAEIIFDQGLGDMFVVRTAGHVIDSAVLGSIEYAVTVLNVPLIV

VLGHDSCGAVNAALAAINDGTLPGGYVRDVVERVAPSVLLGRRDGLSRVD

EFEQRHVHETVAILMARSSAISERIAGGSLAIVGVTYQLDDGRAVLRDHI

GNIGEEV (SEQ ID NO:3, Uniprot Id. No. P9WPJ9). Methods for testing the activity of compounds against carbonic anhydrase proteins, such as these, are known in the art.

"Small molecule" as used herein, is meant to refer to an agent, which has a molecular weight of less than about 6 kDa and most preferably less than about 2.5 kDa. Many pharmaceutical companies have extensive libraries of chemical and/or biological mixtures comprising arrays of small molecules, often fungal, bacterial, or algal extracts, which can be screened with any of the assays of the application. This application contemplates using, among other things, small chemical libraries, peptide libraries, or collections of natural products. Tan et al. described a library with over two million synthetic compounds that is compatible with miniaturized cell-based assays (*J Am Chem Soc* (1998) 120:8565-8566). It is within the scope of this application that such a library may be used to screen for inhibitors (e.g., kinase inhibitors) of any one of the gene products described herein, e.g., cyclin dependent kinases. There are numerous commercially available compound libraries, such as the Chembridge DIVER-Set. Libraries are also available from academic investigators, such as the Diversity set from the NCI developmental therapeutics program. Rational drug design may also be employed.

Compounds useful in the methods of the present invention may be obtained from any, available source, including systematic libraries of natural and/or synthetic compounds. Compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, J. Med. Chem. 37:2678-85, which is expressly incorporated by reference); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, Anticancer Drug Des. 12:145, which is expressly incorporated by reference).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al, (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233, each of which is expressly incorporated by reference.

Libraries of agents may be presented in solution (e.g., Houghten, 1992, Biotechniques 13:412-421), or on beads (Lam, 1991, Nature 354:82-84), chips (Fodor, 1993, Nature 364:555-556), bacteria and/or spores, (Ladner, U.S. Pat. No. 5,223,409), plasmids (Cull et al, 1992, Proc Natl. Acad Sci USA 89:1865-1869) or on phage (Scott and Smith, 1990, Science 249:386-390; Devlin, 1990, Science 249:404-406; Cwiria et al, 1990, Proc. Natl. Acad. Sci. 87:6378-6382; Felici, 1991, J. Mol. Biol. 222:301-310; Ladner, supra., each of which is expressly incorporated by reference).

Peptidomimetics can be compounds in which at least a portion of a subject polypeptide is modified, and the three dimensional structure of the peptidomimetic remains substantially the same as that of the subject polypeptide. Peptidomimetics may be analogues of a subject polypeptide of the disclosure that are, themselves, polypeptides containing one or more substitutions or other modifications within the subject polypeptide sequence. Alternatively, at least a portion of the subject polypeptide sequence may be replaced with a non-peptide structure, such that the three-dimensional structure of the subject polypeptide is substantially retained. In other words, one, two or three amino acid residues within the subject polypeptide sequence may be replaced by a non-peptide structure. In addition, other peptide portions of the subject polypeptide may, but need not, be replaced with a non-peptide structure. Peptidomimetics (both peptide and non-peptidyl analogues) may have improved properties (e.g., decreased proteolysis, increased retention or increased bioavailability). Peptidomimetics generally have improved oral availability, which makes them especially suited to treatment of humans or animals. It should be noted that peptidomimetics may or may not have similar two-dimensional chemical structures, but share common three-dimensional structural features and geometry. Each peptidomimetic may further have one or more unique additional binding elements.

Applications

As elaborated on in more detail below, the compositions described herein are useful in a number of in vitro and in vivo applications. For example, the compositions described herein can be used to treat bacterial infections, such as *Mycobacterium tuberculosis* infections. In some embodiments, the compositions can be used to decontaminate surfaces, e.g., surgical tools or tables, implants, or even donor organs for transplant (e.g., as an antibiotic component of a soaking or perfusion solution).

Pharmaceutical Compositions and Dosages

When employed as pharmaceuticals, the compounds provided herein can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal, intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also provides pharmaceutical compositions which contain, as the active ingredient, a compound provided herein or a pharmaceutically acceptable salt thereof, in combination with one or more pharmaceutically acceptable carriers (excipients). In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, an active compound can be milled to provide the appropriate particle size prior to combining with the other ingredients. If an active compound is substantially insoluble, it can be milled to a particle size of less than 200 mesh. If an active compound is substantially water soluble, the particle size can be adjusted by milling to provide a substantially uniform distribution in the formulation, e.g. about 40 mesh.

The compounds provided herein may be milled using known milling procedures such as wet milling to obtain a particle size appropriate for tablet formation and for other formulation types. Finely divided (nanoparticulate) preparations of the compounds provided herein can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions provided herein can be formulated so as to provide quick, sustained or delayed release of the active ingredient after administration to the patient by employing procedures known in the art.

For preparing solid compositions such as tablets, the principal active ingredient is mixed with a pharmaceutical excipient to form a solid preformulation composition containing a homogeneous mixture of a compound provided herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient provided herein.

The tablets or pills provided herein can be coated or otherwise compounded to provide a dosage farm affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions provided herein can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

In some embodiments, the compounds provided herein are formulated for intravenous administration. Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof.

The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

A nebulizer of the present application can be a jet air nebulizer (e.g., Pari LC Jet Plus or Hudson T Up-draft II), an ultrasonicnebulizer (e.g., MABISMist II), a vibrating mesh nebulizer (e.g., Micro air by Omron) and a Shockwave nebulizer (EvitLabs Sonik LDI20). As used herein, an "aerosol composition" or like grammatical terms means an inhibitor described herein in a form or formulation that is suitable for pulmonary delivery. The aerosol composition may be in the dry powder form, it may be a solution, suspension or slurry to be nebulized, or it may be in admixture with a suitable low boiling point, highly volatile propellant. It is to be understood that more than one inhibitor and optionally other active agents or ingredients may be incorporated into the aerosolized formulation or aerosol composition.

In certain preferred embodiments, an active agent (e.g., an inhibitor described herein) retains more than 50% of its activity after nebulization, preferably more than 70%. In certain preferred embodiments, an active agent (e.g., an inhibitor described herein) more than 50% of its purity after nebulization, preferably more than 70%.

Active agent formulations suitable for use in the present application include dry powders, solutions, suspensions or slurries for nebulization and particles suspended or dissolved within a propellant. Dry powders suitable for use in the present application include amorphous active agents, crystalline active agents and mixtures of both amorphous and crystalline active agents. The dry powder active agents have a particle size selected to permit penetration into the alveoli of the lungs, that is, preferably 10 µm mass median diameter $(MMD)_5$ preferably less than 7.5 µm, and most preferably less than 5 µm, and usually being in the range of 0.1 µm to 5 µm in diameter. The delivered dose efficiency (DDE) of these powders is >30%, usually >40%, preferably >50 and often >60% and the aerosol particle size distribution is about 1.0-5.0 µm mass median aerodynamic diameter (MMAD), usually 1.5-4.5 µm MMAD and preferably 1.5-4.0 µm MMAD. These dry powder active agents have a moisture content below about 10% by weight, usually below about 5% by weight, and preferably below about 3% by weight. Such active agent powders are described in WO 95/24183 and WO 96/32149, which are incorporated by reference herein.

Dry powder active agent formulations are preferably prepared by spray drying under conditions which result in a substantially amorphous powder. Bulk active agent, usually in crystalline form, is dissolved in a physiologically acceptable aqueous buffer, typically a citrate buffer having a pH range from about 2 to 9. The active agent is dissolved at a concentration from 0.01% by weight to 1% by weight, usually from 0.1% to 0.2%. The solutions may then be spray dried in a conventional spray drier available from commercial suppliers such as Niro A/S (Denmark), Buchi (Switzerland) and the like, resulting in a substantially amorphous powder. These amorphous powders may also be prepared by lyophilization, vacuum drying, or evaporative drying of a suitable active agent solution under conditions to produce the amorphous structure. The amorphous active agent formulation so produced can be ground or milled to produce particles within the desired size range.

Dry powder active agents may also be in a crystalline form. The crystalline dry powders may be prepared by grinding or jet milling the bulk crystalline active agent. The active agent powders of the present application may optionally be combined with pharmaceutical carriers or excipients which are suitable for respiratory and pulmonary administration. Such carriers may serve simply as bulking agents when it is desired to reduce the active agent concentration in the powder which is being delivered to a patient, but may also serve to improve the dispersability of the powder within a powder dispersion device in order to provide more efficient and reproducible delivery of the active agent and to improve handling characteristics of the active agent such as flowability and consistency to facilitate manufacturing and powder filling. Such excipients include but are not limited to (a) carbohydrates, e.g., monosaccharides such as fructose, galactose, glucose, D– mannose, sorbose, and the like; disaccharides, such as lactose, trehalose, cellobiose, and the like; cyclodextrins, such as 2-hydroxypropyl-.beta.-cyclodextrin; and polysaccharides, such as raffinose, maltodextrins, dextrans, and the like; (b) amino acids, such as glycine, arginine, aspartic acid, glutamic acid, cysteine, lysine, and the like; (c) organic salts prepared from organic acids and bases, such as sodium citrate, sodium ascorbate, magnesium gluconate, sodium gluconate, tromethamin hydrochloride, and the like; (d) peptides and proteins such as aspartame, human serum albumin, gelatin, and the like; and (e) alditols, such as mannitol, xylitol, and the like. A preferred group of carriers includes lactose, trehalose, raffinose, maltodextrins, glycine, sodium citrate, human serum albumin and mannitol.

The dry powder active agent formulations may be delivered using Inhale Therapeutic Systems' dry powder inhaler as described in WO 96/09085 which is incorporated herein by reference, but adapted to control the flow rate at a desirable level or within a suitable range. The dry powders may also be delivered using a metered dose inhaler as described by Laube et al. in U.S. Pat. No. 5,320,094, which is incorporated by reference herein. Nebulized solutions may be prepared by aerosolizing commercially available active agent formulation solutions. These solutions may be delivered by a jet nebulizer such as the Raindrop, produced by Puritan Bennett, the use of which is described by Laube et al., supra. Other methods for delivery of solutions, suspensions of slurries are described by Rubsamen et al, U.S. Pat. No. 5,672,581. A device that uses a vibrating, piezoelectric member is described in Ivri et al., U.S. Pat. No. 5,586,550, which is incorporated by reference herein.

Propellant systems may include an active agent dissolved in a propellant or particles suspended in a propellant. Both of these types of formulations are described in Rubsamen et al., U.S. Pat. No. 5,672,581, which is incorporated herein by reference. In certain embodiments, an aerosol or nebulization composition can be combined with one or more other aerosol or nebulization treatments, such as sympathomimetics (e.g., albuterol), antibiotics (e.g., tobramycin), deoxyribonucleases (e.g., pulmozyme), anticholinergic drugs (e.g., ipratropium bromide), or corticosteroids.

As described herein, an active agent (e.g., an inhibitor described herein) may be formulated as microparticles. Microparticles having a diameter of between 0.5 and 10 microns can penetrate the lungs, passing through most of the natural barriers. A diameter of less than ten microns is generally required to bypass the throat; a diameter of 0.5 microns or greater is usually required to avoid being exhaled.

In certain embodiments, an active agent (e.g., an inhibitor described herein) is formulated in a supramolecular complex, which may have a diameter of between 0.5 and 10 microns, which can be aggregated into particles having a diameter of between 0.5 and 10 microns.

In other embodiments, an active agent (e.g., an inhibitor described herein) are provided in liposomes or supramolecular complexes appropriately formulated for pulmonary delivery.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound provided herein. The topical formulations can be suitably packaged in tubes of, for example, 100 g which are optionally associated with instructions for the treatment of the select indication.

The formulations may be presented as, for instance, ointments, creams or lotions, gels, eye ointments and eye or ear drops, sprays, impregnated dressings (e.g., bandages or dressings for use in would healing), and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation. In some embodiments, the compounds are formulated for use in the eye. In some embodiments, the compounds are formulated for use in the ear. In some embodiments, the compounds are formulated for use on the skin, e.g., chronic wounds, such as those associated with diabetes or other cardiovascular/circulatory disorders.

In one embodiment, the compounds provided herein are prepared with carriers that will protect the compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions provided herein contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions provided herein contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions provided herein contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses provided herein.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The therapeutic dosage of a compound provided herein can vary according to, for example, the particular use for which the treatment is made, the manner of administration of the compound, the health and condition of the patient, and the judgment of the prescribing physician. The proportion or concentration of a compound provided herein in a pharmaceutical composition can vary depending upon a number of factors including dosage, chemical characteristics (e.g., hydrophobicity), and the route of administration. For example, the compounds provided herein can be provided in an aqueous physiological buffer solution containing about 0.1 to about 10% w/v of the compound for parenteral administration. Some typical dose ranges are from about 1 mg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Methods for Treatment

Also featured herein are therapeutic methods for treating subjects with a variety of infections, such as tuberculosis infections. The methods comprise administering to the subject an inhibitor of the PhoPR regulon, such as any of those described herein, in an amount effective to treat the infection. In some embodiments, the bacteria infecting the subject are identified as expressing one or both of PhoP or PhoR.

In some embodiments, the methods include receiving the results of a test determining that the bacteria infecting the subject are identified as bacteria in which the PhoPR regulon is conserved and, in view of this information, ordering administration of an effective amount of one or more of the inhibitors described herein to the subject. For example, a physician treating a subject can request that a third party (e.g., a CLIA-certified laboratory) to perform a test to determine whether the bacteria infecting the subject are bacteria in which the PhoPR regulon is conserved. The laboratory may provide such information, or, in some embodiments, provide an expression score or value, or a positive or negative result. If the bacteria have the conserved PhoPR regulon, or if the bacteria are identified as tuberculosis, the physician may then administer to the subject one or more of the inhibitors described herein. Alternatively, the physician may order the administration of the inhibitor to the subject, which administration is performed by another medical professional, e.g., a nurse.

In some embodiments, the method can include: requesting a test, or the results of a test, which determines that the bacteria infecting the subject are *Mycobacterium tuberculosis* or bacteria in which the PhoPR regulon is conserved; and administering or ordering administration of an effective amount of an inhibitor described herein to the subject.

A "subject," as used herein, can be any mammal. For example, a subject can be a human, a non-human primate (e.g., monkey, baboon, or chimpanzee), a horse, a cow, a pig, a sheep, a goat, a dog, a cat, a rabbit, a guinea pig, a gerbil, a hamster, a rat, or a mouse. In some embodiments, the subject is an infant (e.g., a human infant).

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment.

The term "preventing" is art-recognized, and when used in relation to a condition, is well understood in the art, and includes administration of a composition which reduces the frequency of, or delays the onset of, symptoms of a medical condition in a subject relative to a subject which does not receive the composition. For example, treatment with an inhibitor described herein may delay the onset of, and/or reduce the severity of symptoms upon onset of, a *Myobacterium tuberculosis* infection in a subject who has been exposed to *Myobacterium tuberculosis*. Exposure to a bacterial infection, such as *Myobacterium tuberculosis*, can be, e.g., close quarters exposure to an infected individual or exposure to bodily fluids (e.g., sputum, saliva, etc.) from an infected individual.

As used herein, "latent tuberculosis" refers to the presence of *Myobacterium tuberculosis* in one or more cells of the infected individual (e.g., has a positive tuberculosis skin test), but the individual does not have an active infection (exhibits one or more signs or symptoms of a TB infection, such as cough, fever, night sweats, weight loss, fatigue, flu-like symptoms, chest pain, shortness of breath, blood in the sputum, etc.).

As used herein, "MDR tuberculosis" or "multi-drug resistant tuberculosis" refers to a form of tuberculosis that is resistant to two or more of the primary drugs (isoniazid and rifampicin) used for the treatment of tuberculosis. As used herein, "XDR tuberculosis" or "extensively multi-drug resistant tuberculosis" refers to a form of tuberculosis resistant to at least isoniazid and rifampicin among the first-line anti-TB drugs, is resistant to any fluoroquinolone and at least one of three injectable second-line drugs, such as amikacin, kanamycin or capreomycin.

The inhibitor compositions can be administered to a subject, e.g., a human subject, using a variety of methods that depend, in part, on the route of administration. The route can be, e.g., intravenous injection or infusion (IV), subcutaneous injection (SC), intraperitoneal (IP) injection, or intramuscular injection (IM).

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

As used herein the term "effective amount" or "therapeutically effective amount", in an is vivo setting, means a dosage sufficient to treat, inhibit, or alleviate one or more symptoms of the disorder being treated or to otherwise provide a desired pharmacologic and/or physiologic effect (e.g., modulate (e.g., enhance) an immune response to an antigen. The precise dosage will vary according to a variety of factors such as subject-dependent variables (e.g., age, immune system health, etc.), the disease, and the treatment being effected.

Suitable human doses of any of the compounds described herein can further be evaluated in, e.g., Phase I dose escalation studies. See, e.g., van Gurp et al. (2008) *Am J Transplantation* 8(8):1711-1718; Hanouska et al. (2007) *Clin Cancer Res* 13(2, part 1):523-531; and Hetherington et al. (2006) *Antimicrobial Agents and Chemotherapy* 50(10): 3499-3500.

Toxicity and therapeutic efficacy of such compositions can be determined by known pharmaceutical procedures in cell cultures or experimental animals (e.g., animal models of infection). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such compounds lies generally within a range of circulating concentrations of the compounds that include the $ED_{50}$ with little or no toxicity. The dosage may vary within this range depending upon the dosage form employed and the route of administration utilized. A therapeutically effective dose can be estimated initially from cell culture assays. A dose can be formulated in animal models to achieve a circulating plasma concentration range that includes the ICso (i.e., the concentration of the inhibitor which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration is desired, cell culture or animal modeling can be used to determine a dose required to achieve a therapeutically effective concentration within the local site. Suitable dosages are described herein.

In some embodiments of any of the methods described herein, an agent can be administered to a mammal in conjunction with one or more additional therapeutic agents. For example, in some embodiments, it may be advantageous to administer an inhibitor described herein in combination with at least one additional pharmaceutical (or therapeutic) agent (e.g., first-line or second-line antituberculosis drugs, and for patients with HIV or AIDS an HIV/AIDS drug). The inhibitor may be administered either simultaneously with, or before or after, one or more other therapeutic agent(s). Alternatively, the compound of the present invention may be administered separately, by the same or different route of administration, or together in the same pharmaceutical composition as the other agent(s).

Suitable additional TB agents include first-line drugs (such as isoniazid, rifampicin, pyrazinamide, ethambutol and combinations thereof); second-line drugs (such as streptomycin, kanamycin, amikacin, capreomycin, ofloxacin, levofloxacin, moxifloxacin, cycloserine, para-aminosaicylic acid, ethioamide, prothionamide, thioacetazone and combinations thereof); and other antituberculosis drugs (such as clofazimine, amoxicilin with clavulanate, imipenem, linezolid, clarithromycin, thioridazine and combinations thereof). Other potential additional TB agents include compounds such as bicyclic nitroimidazoles (e.g., (S)-6,7-dihydro-2-nitro-6-[[4-(trifluoromethoxy)phenyl]methoxy]-5H-imidazo[2,1-b][1,3]oxazine (PA-824) and TBA-354, available from TB Alliance), bedaquiline (TMC-207), delamanid (OPC67683), oxazolidinone, 2-[(2S)-2-methyl-1,4-dioxa-8-azaspiro[4.5]decan-8-yl]-8-nitro-6-trifluoromethyl-4H-1,3-benzothiazin-4-one (BTZ043), imidazopyridines (e.g., Q201, available from Quro Science Inc.), and combinations thereof.

Suitable therapeutic agents for adjunct therapy include human immunodeficiency virus (HIV) drugs, immunotherapeutic agents, (e.g., anti-interleukin 4 neutralizing antibodies, high-dose intravenous immunoglobulin, 16a-bromoepiandosterone (HE2000), RUTI® vaccine, DNA vaccine with HSP65, Ag85, MPT-64, and MPT-83, dzherelo (plant extracts from the Ukraine), cytokines (such as Interleukin 2, Interleukin 7, Interleukin 15, Interleukin 27, Interleukin 12, Interferon γ), immunosuppressive agents (such as corticosteroids, thalidomide, and etanercept)), steroids, anti-inflammatory agents (e.g. prednisone), and other agents well-known to those of skill in art for use in improving the quality of care for patients being treated for the diseases, conditions, or disorders described herein.

Suitable HIV/AIDS drugs include non-nucleoside reverse transcriptase inhibitors (NNRTIs), such as efavirenz (Sustiva), etravirine (Intelence) and nevirapine (Viramune); Nucleoside reverse transcriptase inhibitors (NRTIs), such as Abacavir (Ziagen), and the combination drugs emtricitabine and tenofovir (Truvada), and lamivudine and zidovudine (Combivir); Protease inhibitors (Pis), such as atazanavir (Reyataz), darunavir (Prezista), fosamprenavir (Lexiva) and ritonavir (Norvir); Entry or fusion inhibitors, such enfuvirtide (Fuzeon) and maraviroc (Selzentry); and Integrase inhibitors, such as Raltegravir (Isentress).

Methods for diagnosing a subject has having tuberculosis are well known in the art and include, e.g., chest x-ray, testing of a sputum sample, tuberculin skin test, or a blood test (e.g., to test for the presence of microbial DNA or circulating anti-TB antibodies).

Likewise, methods for determining whether bacteria express PhoP and/or PhoR are known in the art and include, e.g., protein (e.g., Western blot, dot blot, or other immunoassays) and nucleic acid (e.g., RT-PCR) detection techniques.

The International Standards for Tuberculosis Care describes a widely accepted level of care that all practitioners, public and private, should follow in dealing with people who have, or are suspected of having, tuberculosis. The Standards are intended to facilitate the effective engagement of all care providers in delivering high-quality care for patients of all ages, including those with sputum smear-positive, sputum smear—negative, and extrapulmonary tuberculosis; tuberculosis caused by drug resistant *Mycobacterium tuberculosis* complex (*M. tuberculosis*) organisms; and tuberculosis combined with human immunodeficiency virus (HIV) infection, all of which are amenable to treatment using one or more of the inhibitors described herein.

Another aspect of the disclosure is a product comprising an inhibitor described herein and at least one other therapeutic agent (or pharmaceutical agent) as a combined preparation for simultaneous, separate or sequential use in therapy to treat a subject having sputum smear-positive, sputum smear-negative, and extrapulmonary tuberculosis; tuberculosis caused by drug resistant *Mycobacterium tuberculosis* complex (*M. tuberculosis*) organisms; or tuberculosis combined with human immunodeficiency virus (HIV) infection.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Example 1. Materials and Methods

Bacterial Strains and Growth Conditions

Mtb experiments, unless otherwise stated, were performed with Mtb strain CDC1551. The phoP::Tn and ΔphoPR mutants have been previously described (5, 14). Cultures were maintained in standing tissue culture flasks in 7H9 Middlebrook medium supplemented with 10% OADC and 0.05% Tween-80 and incubated at 37° C. with 5% $CO_2$.

High-Throughput Screening Assay and Data Analysis

A compound library (of approximately 220,000 compounds) arrayed in 384-well optical microtiter plates was provided by the Institute of Chemistry and Cell Biology (ICCBL) at Harvard University. Two columns of each plate were left blank for positive and negative controls of 0.3 μM rifampicin and DMSO, respectively. The CDC1551(aprA'::GFP) fluorescent reporter was grown in Middlebrook 7H9 medium, buffered at pH 7.0 with 100 mM MOPS, to mid- to late-log phase. The cultures were then pelleted, re-suspended in 7H9 buffered at pH 5.7 with 100 mM MES and dispensed into the 384-well assay plates at an OD of 0.2. The plates were incubated for 6 days at 37° C. and both fluorescence and optical density (OD) were measured on a plate reader. For analysis of hits, fluorescence and growth inhibition were normalized based on the rifampin (100%) and DMSO (0%) controls, respectively. Potential PhoPR regulon inhibitors were flagged as compounds that had: i) greater than 35% fluorescence inhibition, and ii) at least a 1.5-fold greater fluorescence inhibition as compared to growth inhibition.

For $EC_{50}$ determinations, Mtb CDC1551 aprA'::GFP was grown to mid- to late-log phase in non-inducing medium (7H9, pH 7.0), pelleted, and re-suspended in GFP inducing medium (7H9, pH 5.7) in the presence of a 14-point dilution series (2.5-fold) of ETZ at a final concentration ranging from 3 nM to 500 μM. $EC_{50}$ values were calculated based on a variable slope, four-parameter non-linear least squares regression model in the GraphPad Prism software package (ver. 6).

Transcriptional Profiling and Data Analysis

Figure 8:
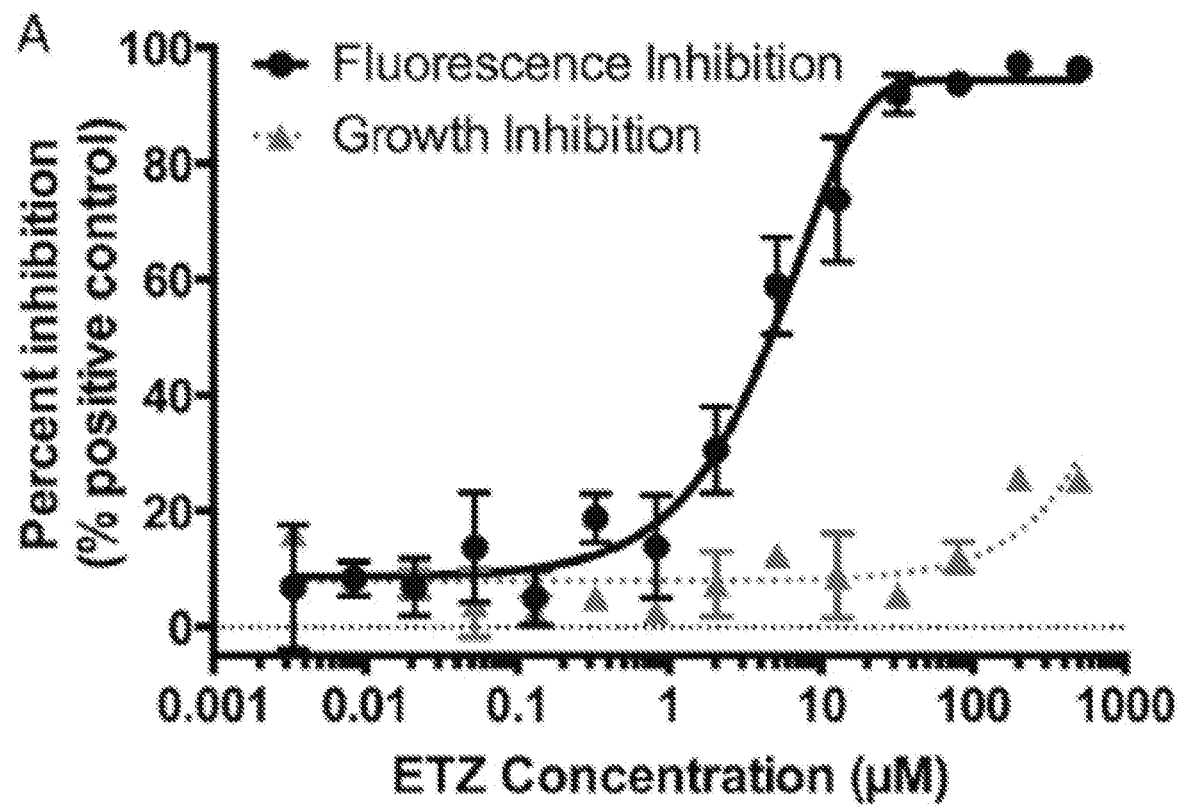
FIG. 8 includes three panels, A-C, and depicts ETZ inhibition of the phoPR regulated aprA'::GFP in a dose dependent manner, but does not alter the pH of the medium or macrophage phagosome acidification. (Panel A) ETZ inhibits PhoPR-dependent aprA'::GFP fluorescence in a concentration dependent manner at pH 7.0 with an EC50 of 4.7 µM and little effect on growth. (Panel B) The pH of the culture medium is not altered when Mtb is treated with ETZ (80 µM) compared to a DMSO control after 6 days incubation at pH 5.7. (C) pHrodo labeled particles (Life Technologies) were fed to BMDMs pre-treated for 4 hours with: ETZ (100, 80, or 40 µM) or an equivalent volume of DMSO. Concanamycin A (CcA, 100 nM) inhibits phagosome acidification through inhibition of the vacuolar ATPase and added 30 minutes before feeding of labeled particles. pHrodo fluorescence increases as pH decreases and was monitored every 5 minutes for 100 minutes. Treatments were present throughout the assay. F0: fluorescence at time 0. F: fluorescence at each time point. Error bars represent the standard deviation from at least three technical replicates. Data are representative of at least two biological replicates. Error bars are the standard deviation of at least 3 technical replicates.
Figure 8:
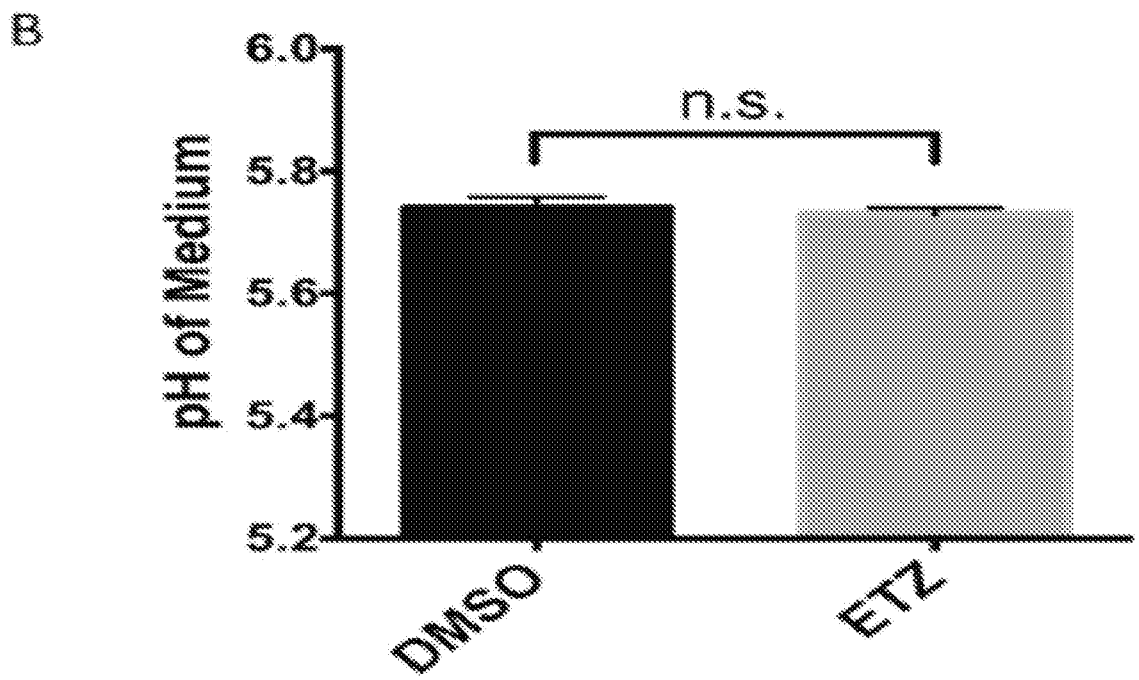
Figure 8:
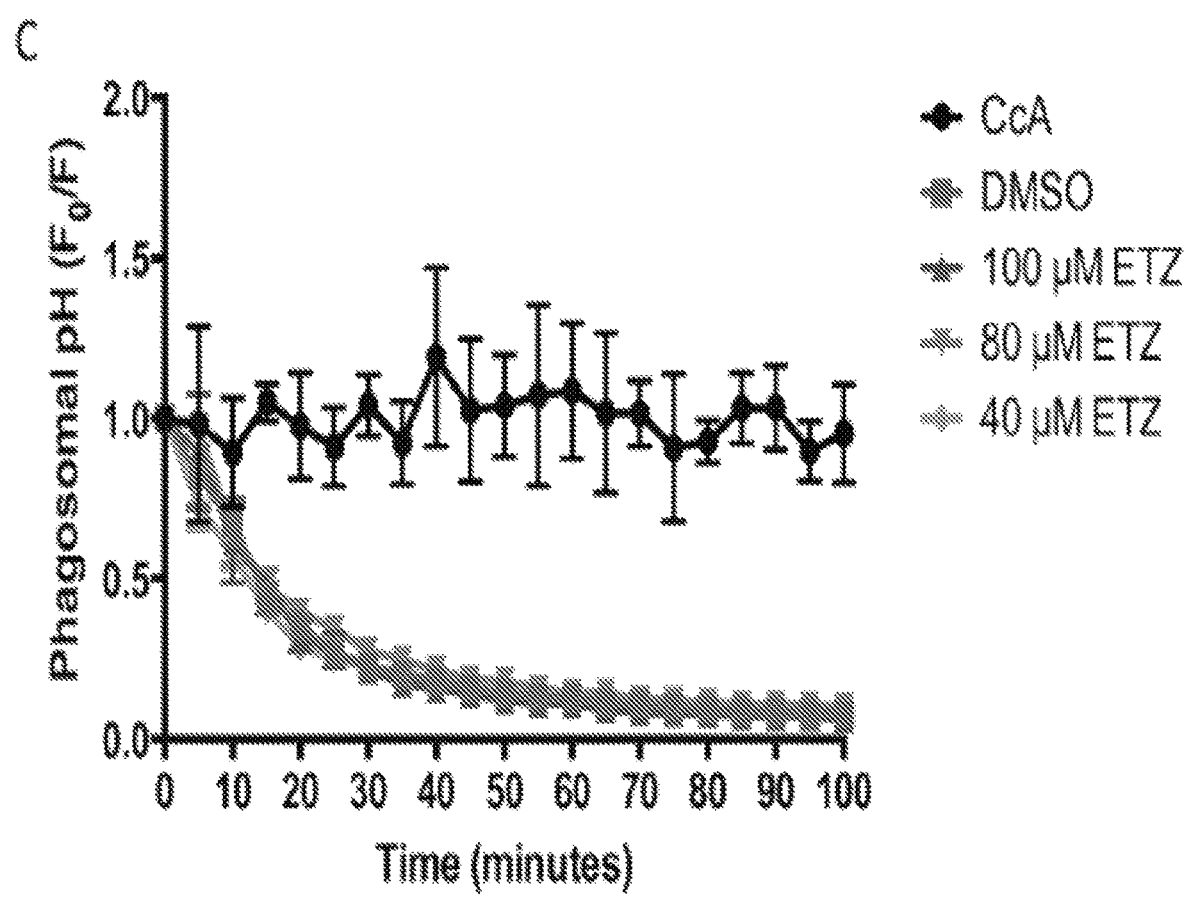

For RNA-seq experiments, Mtb cultures were grown at 37° C. in T-25 vented, standing tissue culture flasks in 8 mL of buffered 7H9 medium seeded at an initial OD of 0.2. Three conditions were examined with two biological replicates: 1) DMSO treated, pH 7.0, 2) DMSO treated, pH 5.7, and 3) 40 μM ETZ treated, pH 5.7. The phoP::Tn mutant was grown in a similar manner and treated with DMSO at pH 5.7. Following six days incubation, total bacterial RNA was extracted as previously described (2). RNA-sequencing, data analysis and qPCR were performed as described by Baker et al. (15) with minor modifications (FIG. 8). The transcriptional profiling data have been submitted to the NCBI GEO database (accession number: GSE63917).

Cell Culture

Primary murine bone marrow derived macrophages (BM-DMs) were isolated and grown as described (16). Briefly, BMDMs were isolated from WT C57Bl/6 mice (Charles River) and grown at 37° C. (5% $CO_2$) in DMEM (Corning CellGro) containing 10% fetal bovine serum (Thermo Scientific), 20% L-cell conditioned medium, 1 mM pyruvate, 2 mM L-glutamine, and 1 mM penicillin/streptomycin (Corning CellGro). Cells were grown until fully differentiated, scraped, and plated in medium lacking antibiotics at either $1\times10^5$ cells/mL for macrophage infections or $2\times10^5$ cells/mL for measuring phagosome acidification. Cells were allowed to adhere overnight before addition of Mtb or experimental treatments.

Carbonic Anhydrase Activity Assay

Carbonic anhydrase (CA) activity was measured using a modified Maren endpoint method (17) based on acidification of the media by CA conversion of $CO_2$. WT Mtb CDC1551 cultures were grown for six days at 37° C. in T-150 vented, standing tissue culture flasks in 50 mL of 7H9 medium seeded at an initial OD of 0.2. Two conditions were examined: 1) DMSO treated, pH 5.7, and 2) ETZ treated (80 µM), pH 5.7. Cells were then were pelleted, washed once in cold assay buffer (20 mM Tris, 20 mM NaCl, pH 8.3), re-suspended in 500 µL cold assay buffer and transferred to 2 mL screw cap tubes containing 200 µL of 0.1 mm glass beads. Cell lysis was achieved by bead beating at max speed for 2 minutes. Lysates were clarified by centrifugation at 21,000×g for 1 minute. Clarified lysates were transferred to new tubes and kept on ice. The CA assay apparatus utilized: 15×88 mm Pyrex glass tubes, 14 mm serum stoppers, 18 gauge 1.5 inch needles, 1 mL syringes, 1 mm tubing, sample evaporator needles, and 0.22 µm syringe filters (to prevent aerosol escape). All assay components were kept on ice before and during the assay. 450 µL of dd$H_2O$ was added to the tube with 50 µL cell lysate. $CO_2$ was bubbled in at a constant rate and 500 µL of cold color indicator buffer (20 mM imidazole, 5 mM Tris, 0.2 mM 4-nitrophenol) was added, and timing was initiated. The color was monitored until clearing, comparing it to a previously cleared sample. Data are representative of at least two biological replicates with similar findings in each experiment.

Cytoplasmic pH and Phagosome Acidification Measurement

Cytoplasmic pH was measured as previously described by Purdy et al. (18). WT Mtb CDC1551 was grown in a similar manner as the transcriptional profiling experiments. Four conditions were examined: 1) DMSO treated, pH 7.0, 2) DMSO treated, pH 5.7, 3) 80 µM ETZ, pH 7.0, and 4) 80 µM ETZ, pH 5.7. Cytoplasmic pH was measured following 6 days incubation. Phagosome acidification was measured using pHrodo labeled beads (Life Technologies) fed to BMDMs in a 96-well black assay plate. One column did not contain any cells for a media and beads only control. Five conditions were examined: 1) 100 µM ETZ, 2) 80 µM ETZ, 3) 40 µM ETZ, 4) 100 nM Concanamycin A (CcA), and 5) an equivalent volume of DMSO. Cells were pre-treated for 4 hours with ETZ and DMSO before addition of particles. CcA was added 30 minutes prior to assay initiation. pHrodo green labeled particles (ex. 509 nm, em. 533 nm) were added to each well in pre-warmed live cell imaging solution (Life Technologies) at 1 mg/mL. The assay was carried out in a Perkin Elmer plate reader at 37° C. for 100 minutes taking readings at 5-minute intervals.

Analysis of Mycobacterial Lipids

Figure 10:
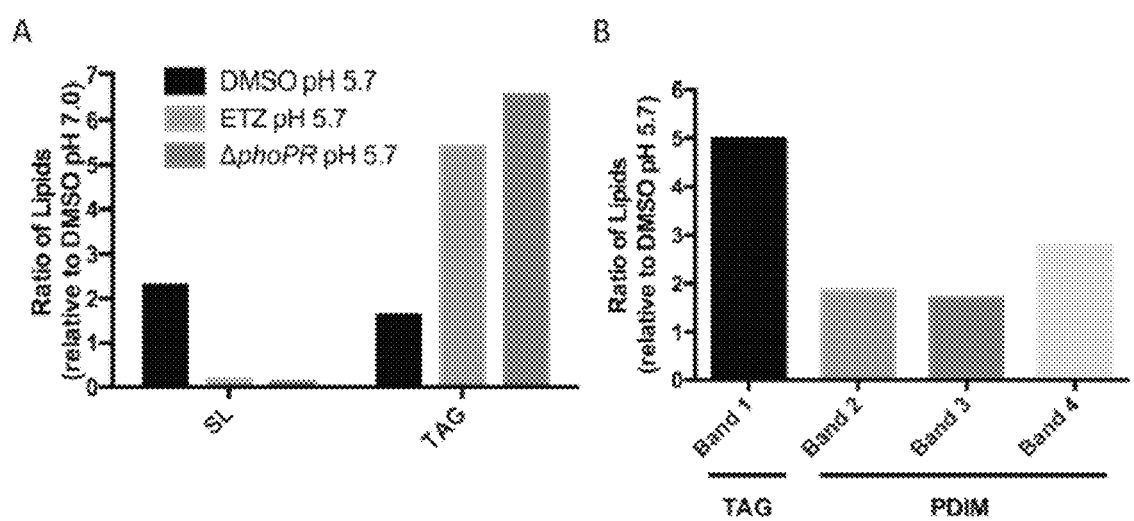
FIG. 10 includes three panels, A-C, and depicts the alteration of lipid species production by ETZ. (Panels A and B) Quantitation of lipid analysis as summarized in FIG. 3. (Panel C) Radio-TLC showing Mtb treated with 80 µM ETZ and the ΔphoPR mutant strain exhibit a lack of accumulation of sulfolipid (SL) (*), consistent with that of a SL standard. The unlabeled SL standard was resolved on the same TLC plate as radio-labeled lipids, and visualized by staining with phosphomolybdic acid and charring. Data are representative of two biological replicates with similar findings in each experiment.
Figure 10:
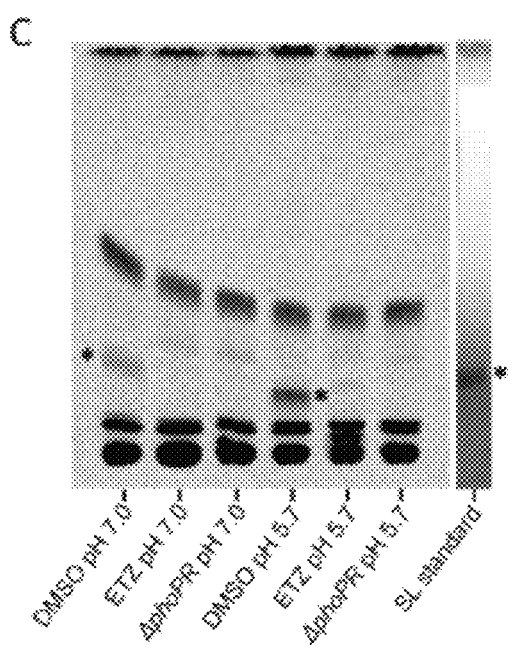

Lipid analysis was conducted as previously described (15). Briefly, Mtb cultures were grown at 37° C. in standing, vented T-75 tissue culture flasks in 40 ml of minimal medium supplemented with 10 mM pyruvate and seeded at an initial OD of 0.1. Four conditions were examined: 1) DMSO treated, pH 7.0, 2) DMSO treated, pH 5.7, 3) 80 µM ETZ, pH 7.0, and 4) 80 µM ETZ, pH 5.7. Following 3 days incubation, lipids were radiolabeled by adding 8 µCi of [1,2 $^{14}C$] sodium acetate to each culture. Following 6 days of labeling, the lipids were extracted and analyzed by thin layer chromatography (TLC). Total extractable lipid $C^{14}$ incorporation was determined using a scintillation counter. To analyze lipid species, 20,000 counts per minute (CPM) were loaded at the origin of a 100 $cm^2$ high performance TLC silica gel 60 aluminum sheet. To separate SL and TAG, TLCs were developed with the chloroform:methanol:water (90:10:1 v/v/v) and hexane:diethyl ether:acetic acid (80:20:1, v/v/v) solvent systems, respectively (15). To examine PDIM accumulation the 2D TLC was developed with 1) petroleum ether:ethyl acetate (98:2, v/v) and 2) petroleum ether:acetone (98:2, v/v) (5). Radiolabeled lipids were detected with a phosphor screen and Typhoon Imager and quantified using ImageJ software (19). Radiolabeling experiments, lipid extractions and analyses were repeated in two independent biological replicates with similar findings in both replicates. TAG and PDIM species were previously identified using these solvent systems and mass spectroscopy(5). SL identity was confirmed using a SL standard (provided by BEI resources) that was visualized by staining with phosphomolybdic acid followed by charring (FIG. 10, Panel C).

Analysis of Esx-1 Protein Export

*Mycobacterium tuberculosis* Erdman and Δesat-6 strains were a gift from Jeffery S. Cox (20). Mtb was cultured in 7H9 medium, collected by centrifugation, washed once with 5 mL of Sauton's broth and re-suspended in 50 mL of Sauton's broth in the presence or absence of 80 µM ETZ. After 5 days of growth at 37° C., the cells were diluted, washed and treated as above. The cultures were grown at 37° C. with gentle shaking for 4 days. Lysates were prepared as described previously (20). The secreted protein fraction was concentrated using Amicon filter systems with a 3 kDa molecular weight cut-off and total protein concentrations were determined by the MicroBCA assay (Promega). 13.5 µg of cell lysates and culture filtrates were separated on a 4-20% pre-cast gel (Bio-Rad) and transferred to nitrocellulose. Nitrocellulose membranes were incubated with antibodies against Esat-6 (Abcam, ab26246), CFP-10, MPT32, or RNAPβ (Abcam, 8RB13) and detected using chemiluminescence (LumiGLO®)(21). The following reagents were obtained through BEI Resources, NIAID, NIH: Polyclonal Anti-*Mycobacterium tuberculosis* CFP10 (Gene Rv3874) (antiserum, Rabbit), NR-13801, Polyclonal Anti-*Mycobacterium tuberculosis* Mpt32 (Gene Rv1860) (antiserum, Rabbit), NR-13807.

Macrophage Infections

Macrophage infections were performed as described (16). Briefly, BMDMs were infected at an MOI of 1:1 with Mtb CDC1551 in 24-well tissue culture treated plates. Infected BMDMs were treated with 80 µM ETZ or an equivalent volume of DMSO every two days for 9 days total. At days 3, 6 and 9, intracellular bacteria were quantified by lysing macrophage monolayers and performing serial dilution plating of lysates on 7H10 agar. For fluorescence microscopy experiments, macrophages were seeded on glass coverslips before infection with Mtb CDC1551(aprA'::GFP smyc':: mCherry). Samples were treated every two days with 100

μM ETZ or an equal volume of DMSO for 9 days. Monolayers were then fixed in 4% paraformaldehyde and imaged by confocal microscopy. Survival assays and imaging experiments were repeated with three biological replicates with similar results.

Quantitative Single-Cell Imaging of Mtb Exposure to ETZ in Mice

Figure 11:
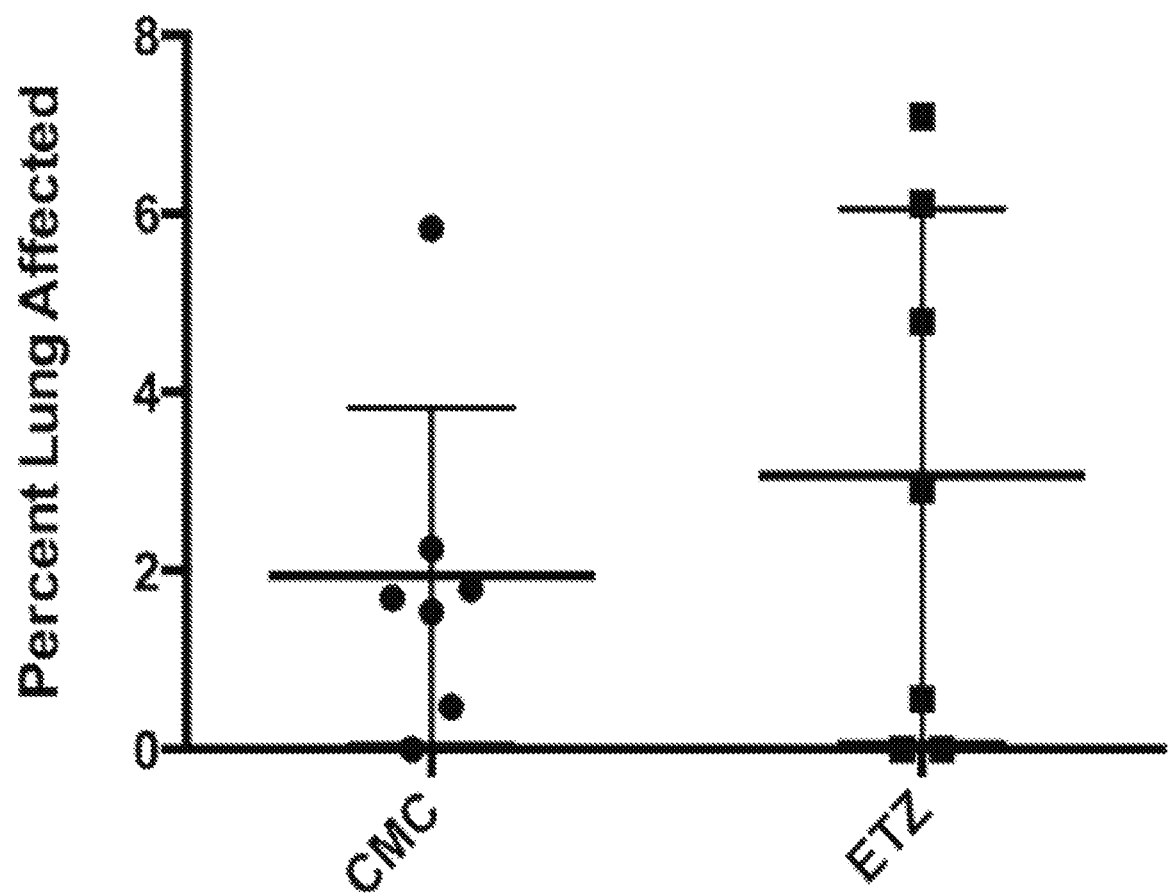
FIG. 11 depicts a comparison of percent lung area affected of the section examined for each CMC and ETZ treated animal. There is no significant difference between the two groups.

C57BL/6 mice were infected via the intranasal route with 1000 CFU of the Erdman (aprA'::GFP smyc'::mCherry) dual fluorescent reporter. Mice were treated with 100 mg/kg of ETZ or an equal volume of 0.25% carboxymethyl cellulose (CMC) 5 days per week for 4 weeks via oral gavage. After 4 weeks, the right lung was homogenized and plated for enumeration of the bacterial load and the left lung was fixed in 4% paraformaldehyde before being transferred to 30% sucrose for confocal microscopy and pathology evaluation (FIG. 8). This experiment was repeated and the data from the two independent biological replicates were similar and therefore combined. Lungs were also examined for histopathological hallmarks of TB disease (FIG. 8), however, ETZ treated lungs did not have a significant reduction in the area of the lung showing Mtb-associated granulomatous pneumonia (FIG. 11). Mice were euthanized by carbon dioxide asphyxiation followed by cervical dislocation. Animal experiments were conducted following protocols approved by the Michigan State University Institutional Animal Care and Use Committee.

pH of Medium Determination

To examine whether ETZ alters the pH of the medium, WT Mtb CDC1551 was grown in a similar manner as the transcriptional profiling experiments. Two conditions were examined: 1) DMSO treated, pH 5.7 or 2) 80 μM ETZ treated, pH 5.7. After 6 days incubation, cells were pelleted and supernatants were collected and filtered twice through 0.22 μm filters. The pH of the supernatants was then measured on a pH meter.

Data Analysis of RNA-Seq Transcriptional Profiling Experiments

Differential gene expression was calculated by normalizing data utilizing the trimmed mean of M-values normalization method (Robinson et al. (2010) *Genome Biol*:R25) and filtering genes that had >2 average normalized counts per million (CPM) within the edgeR package (Robinson et al. (2010) *Bioinformatics* 26:139-140). Statistical analysis was performed in RStudio (ver. 0.97.551) by fitting an additive generalized linear model (McCarthy et al. (2012) *Nucleic Acids Res* 40:4288-4297) or exact test (Robinson et al. (2008) *Biostatistics* 9:321-332) with the negative binomial distribution for each set of conditions and testing for differential gene expression utilizing the edgeR package. Differentially expressed genes were determined to be statistically significant based on >2-fold differentially regulated and an adjusted p<0.05.

Confocal Microscopy and Pathology of ETZ Treated Lungs

PFA fixed mouse lungs were frozen in a 30% sucrose PBS pH 7.4 solution, frozen in a dry ice, ethanol bath, and stored at −80° C. until imaging. At the time of imaging, lungs were thawed and hand-sectioned using a sterile scalpel. Sections were transferred to a microscope slide and 10 μL of ProLong® Gold antifade reagent (Invitrogen) was added. Samples were then mounted on a glass coverslip and imaged immediately. Images were obtained using an Olympus FV1000 confocal microscope. Settings for GFP and mCherry fluorescence were held constant through the image acquisition to allow for comparison between samples. For quantification of Mtb reporter fluorescence, bacilli were identified in the mCherry channel and the corresponding sum of GFP fluorescence was measured using the Volocity software package (Perkin Elmer). At least 1500 bacilli were counted across multiple fields of view and lungs.

For histopathology, transverse sections of each lung specimen was fixed in 4% paraformaldehyde for 48 hours, transferred to 50% ethanol for 4 hours, processed routinely, embedded in paraffin, and sectioned at 4 μm, followed by routine hematoxylin and eosin staining. Photomicrographs were acquired, and using Image-J the total area of each lung section was measured, as was the area of each lesion and a percentage of lung affected was calculated from this data.

Example 2. Results

Identification of Ethoxzolamide as an Inhibitor of the PhoPR Regulon

A whole-cell phenotypic screen was employed to identify inhibitors of the PhoPR regulon. The CDC1551(aprA'::GFP) fluorescent reporter exhibits pH-inducible fluorescence that is fully dependent on PhoPR (5). Although PhoPR is required for growth in vivo, a PhoPR mutant grows well in rich medium at acidic pH; therefore, compounds that inhibit pH-inducible reporter fluorescence, but not growth, are anticipated to be inhibitors of the PhoPR pathway. To discover inhibitors of the PhoPR regulon a high throughput screen (HTS) of a ~220,000 compound library composed of small molecules representing broad chemical diversity was performed. The reporter strain was grown in 384 well plates containing the compound library (at an concentration of ~10 μM) in rich medium buffered at pH 5.7. Following 6 days of incubation, plates were examined for GFP fluorescence and growth. Ethoxzolamide (ETZ, FIG. 1, Panel A) was identified as a compound that inhibits Mtb reporter fluorescence but that does not reduce growth. ETZ inhibits CDC1551 (aprA'::GFP) reporter fluorescence with a half-maximal effective concentration ($EC_{50}$) of 5.6 μM at pH 5.7, (FIG. 1B). Growth was mostly unaffected at pH 5.7 across the range of ETZ concentrations tested (FIG. 1, Panel B). Basal aprA expression is also dependent on PhoPR at neutral pH and we observed inhibition of reporter fluorescence at pH 7.0 with a similar $EC_{50}$ of 4.7 μM (FIG. S1A). ETZ is a carbonic anhydrase (CA) inhibitor that has previously been shown to inhibit recombinant Mtb CA proteins (22).

Whether ETZ inhibits Mtb CA activity was examined, and full inhibition of CA activity in Mtb whole cells treated with ETZ for 6 days was observed (FIG. 1, Panel C). ETZ did not quench GFP fluorescence, alter the pH of the culture medium (FIG. 8, Panel B) and only caused a slight acidification of cytoplasmic pH (FIG. 1, Panel D). These data support two novel findings: 1) ETZ inhibits the PhoPR regulon, and 2) a previously unrecognized link may exist between Mtb CA activity and PhoPR signaling.

Figure 2:
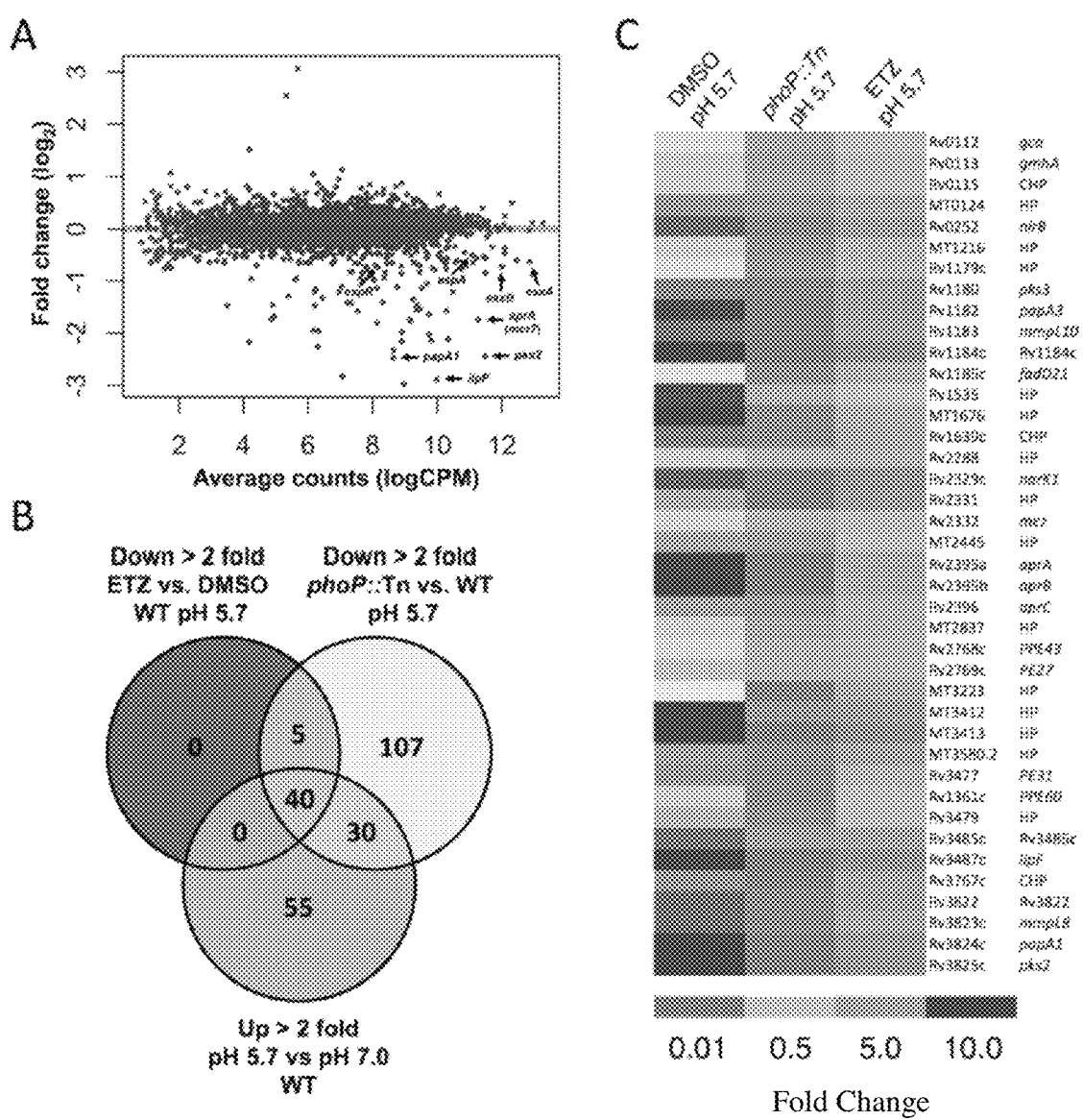
FIG. 2 includes three panels, A-C, and depicts ETZ inhibition of the core PhoPR regulon. (Panel A) RNA-seq transcriptional profiling shows PhoPR- regulated genes are significantly down-regulated when treated with ETZ at acidic pH compared to the DMSO control pH 5.7. (Panel B) A complete overlap is observed between genes down-regulated (>2-fold, p<0.05) by ETZ treatment and the mock treated phoP::Tn mutant strain. Forty of these genes are also induced at pH 5.7 as compared to pH 7.0 (>2-fold, P<0.05). (Panel C) A list of the forty acidic pH induced and PhoPR and ETZ repressed (>2-fold, p<0.05) genes. CHP: conserved hypothetical protein; HP: hypothetical protein.
Figure 9:
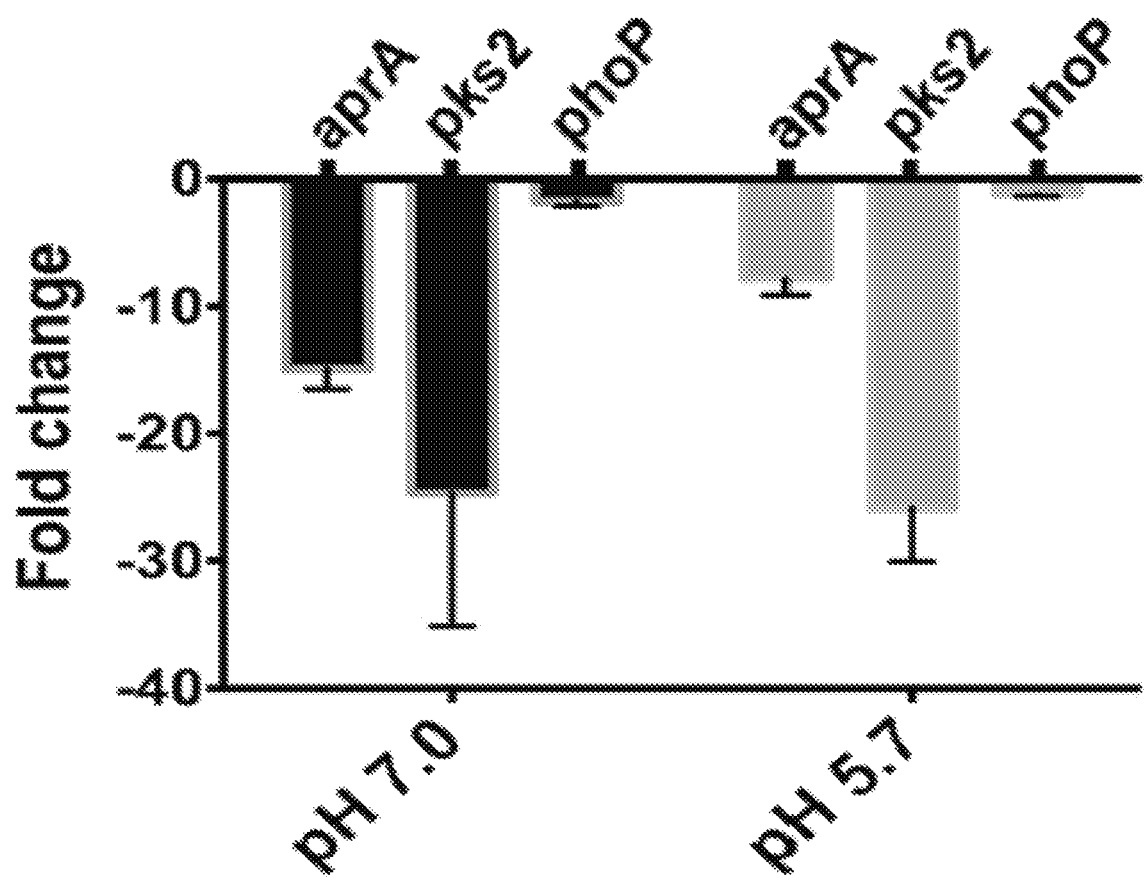
FIG. 9 depicts ETZ down-regulation of PhoPR regulon genes, but not phoP. Semi-quantitative RT-PCR validation of RNA-seq transcriptional profiling reveals that ETZ down-regulates PhoPR-regulated genes (aprA and pks2), but not phoP. Error bars are the standard deviation of three technical replicates. Data are representative of three biological replicates.

Prior transcriptional profiling and ChIP-seq studies have defined a core regulon that is directly regulated by PhoP and induced by acidic pH (2-5, 23, 24). To determine if ETZ inhibits the PhoPR regulon, RNA-seq transcriptional profiling was performed. Mtb CDC1551 was inoculated into rich medium buffered at pH 5.7 in the presence of either 40 μM ETZ or an equivalent volume of DMSO. As a positive control for PhoPR-regulated genes, a DMSO treated phoP transposon mutant strain (phoP::Tn) was cultured using the above described conditions. To identify genes regulated by acidic pH, the transcriptional profile of DMSO treated Mtb at pH 5.7 as compared to pH 7.0. After 6 days incubation, total RNA was isolated and subjected to RNA sequencing. ETZ treatment of Mtb caused the down-regulation (>2-fold, p<0.05) of 45 genes (FIG. 2, Table 2). All 45 of these genes were also down-regulated in the phoP::Tn mutant and 40 were induced by acidic pH (FIG. 2, Panels B and C). ETZ down-regulated genes include many genes previously shown to be directly controlled by PhoP and are involved in lipid synthesis, carbon metabolism, and virulence (FIG. 2, Panel C) (23, 24). Many of the remaining 137 genes down-regulated in the phoP::Tn mutant but not by ETZ (>2-fold, p<0.05), are significantly downregulated by ETZ but less than 2-fold (e.g. espR, espA, esxA, FIG. 2, Pan). To confirm the RNA-seq results, semi-quantitative real-time PCR was conducted on the phoP gene and two well-characterized PhoP regulated genes, aprA and pks2. In ETZ treated Mtb, aprA and pks2 were down-regulated >5 fold at both pH 7.0 and 5.7 (FIG. 9). phoP did not exhibit substantial differential regulation by ETZ, demonstrating that ETZ is not acting by modulating phoP gene expression. These findings validate ETZ as an inhibitor of the core PhoPR regulon.

Lipid Synthesis and Esx-1 Protein Secretion are Modulated by Ethoxzolamide.

Figure 3:
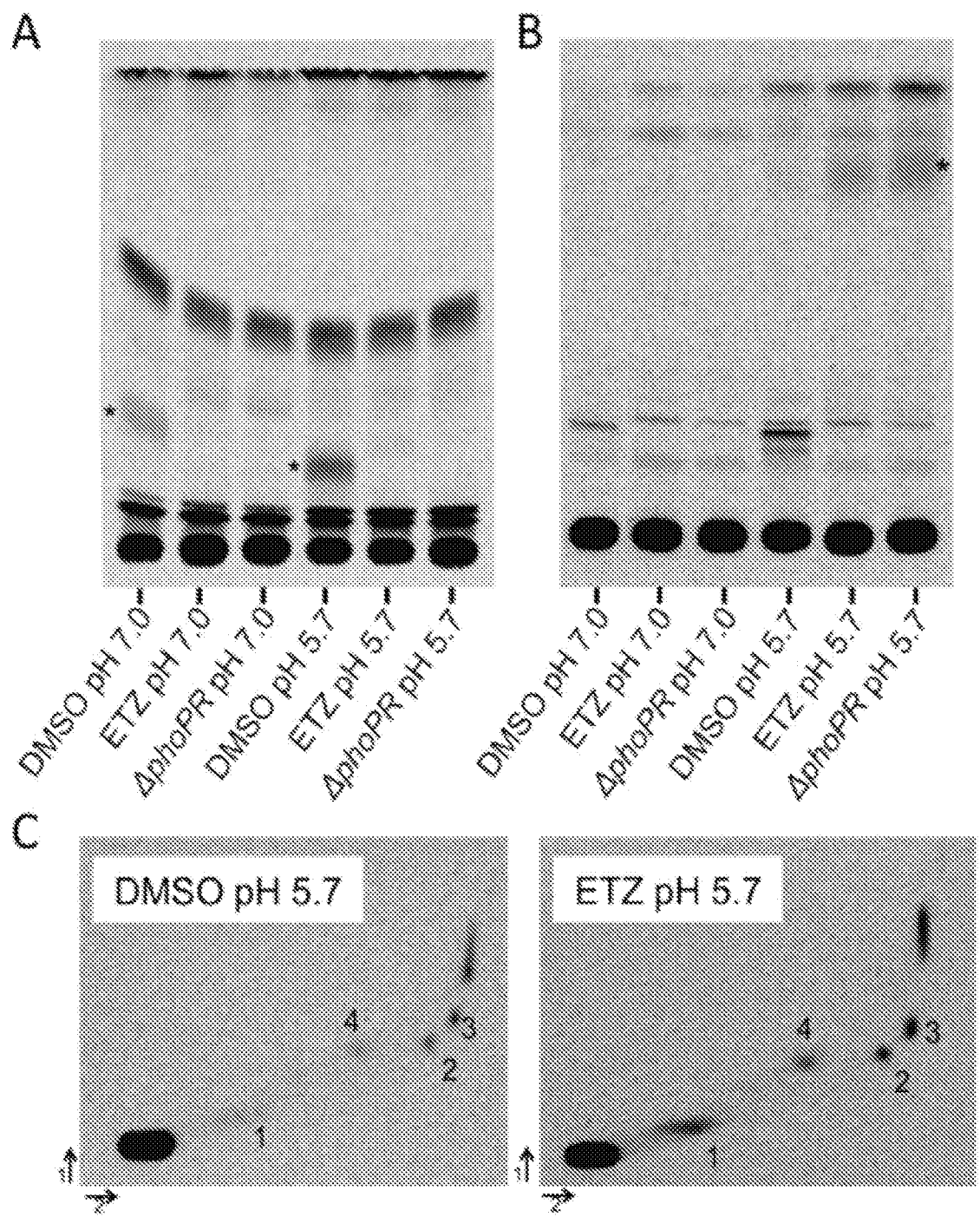
FIG. 3 includes three panels, A-C, and depicts Mtb lipid synthesis being modulated by ETZ. (Panel A) Radio-TLC showing Mtb treated with 80 µM ETZ and the ΔphoPR mutant strain exhibit a lack of accumulation of SL (*) and (Panel B) enhanced accumulation of TAG (*). (Panel C) 2-D radio-TLC demonstrating ETZ treatment increases the accumulation of TAG (spot 1) and phthiocerol dimycocerosate (PDIM) species (spots 2-4) at pH 5.7 compared to a DMSO control. Data are representative of two biological replicates with similar findings in both experiments.

PhoPR controls cell envelope lipids and Esx-1 dependent secretion of ESAT-6 (EsxA)(25, 26). Therefore, whether ETZ modulates these virulence factors was investigated. The PhoPR-dependent mmpL8-pks2 operon (Rv3823c-Rv3825c) is responsible for the production of sulfolipid (SL) and is strongly induced at acidic pH (3, 15, 27, 28). Transcriptional profiling data demonstrated a ~5-fold down-regulation of this operon when treated with ETZ at acidic pH (FIG. 2C), suggesting that similar to a phoPR knockout mutant (ΔphoPR), ETZ may downregulate the accumulation of SL. To test this hypothesis, $^{14}$C radiolabeled lipids were isolated from wild type (WT) and ΔphoPR mutant strains grown at pH 7.0 and pH 5.7 treated with either ETZ or an equal volume of DMSO. A lipid migrating with a position consistent with SL was induced ~2.5 fold at pH 5.7 as compared to pH 7.0 in DMSO, whereas, this lipid was not detected in ETZ treated cells and the ΔphoPR mutant (FIG. 3, Panel A, FIG. 10, Panels A and C). It has been shown previously that mutant strains with reduced accumulation of PhoPR-regulated lipids compensate by over-accumulating other long chain fatty acids, such as triacylglycerol (TAG) and phthiocerol dimycoserate (PDIM) (5, 15, 29). At pH 5.7, as compared to the DMSO control, TAG was induced 5.5-fold and 6.5-fold in ETZ treated Mtb and the ΔphoPR mutant strain, respectively (FIG. 3, Panel B, FIG. 10, Panel A). Similarly, at pH 5.7, a 2-fold increase in the accumulation of PDIM species in the ETZ treated samples as compared to the DMSO treated cells (FIG. 3, Panel C) was observed. Therefore, ETZ treatment phenocopies the ΔphoPR mutant strain for alteration of lipid species production.

Figure 4:
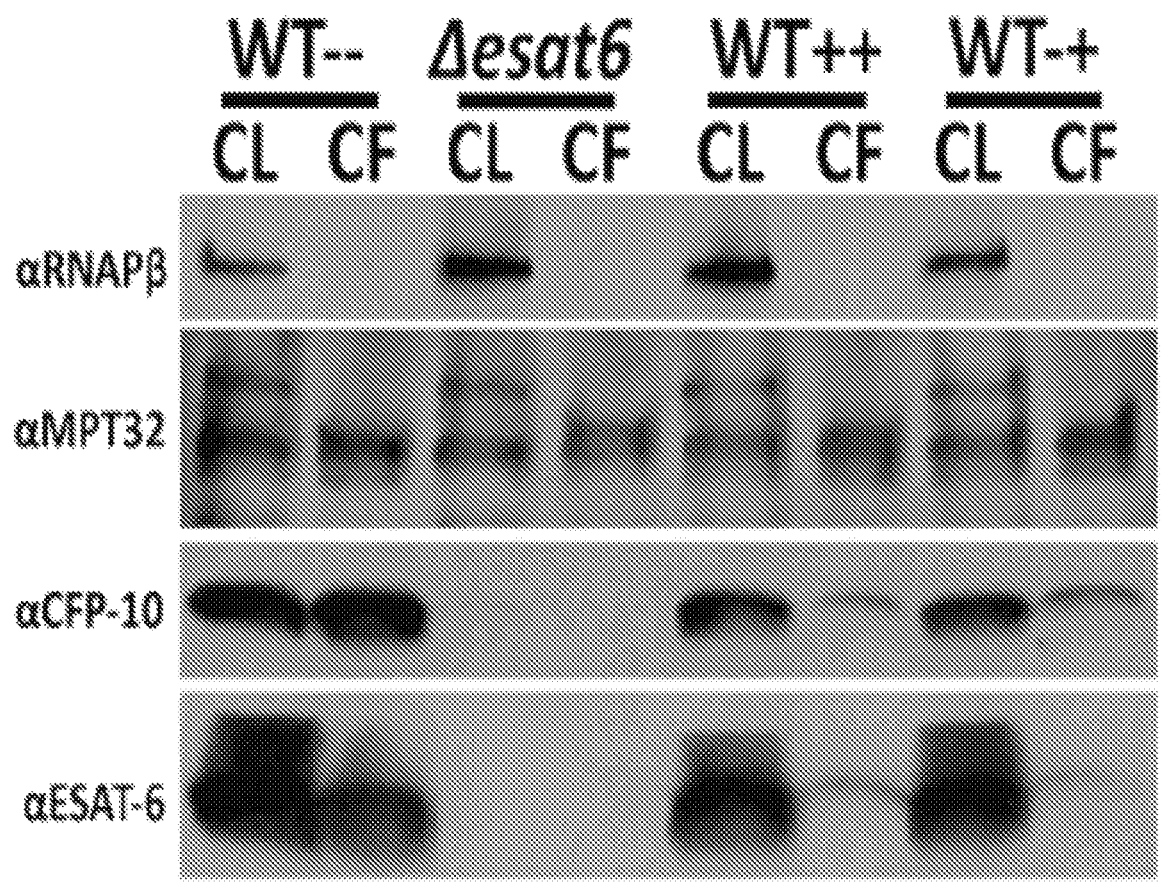
FIG. 4 depicts ETZ treatment inhibits Esx-1 protein export. Western blot analysis of cell lysates (CL) and culture filtrates (CF) of wild-type (WT) *M. tuberculosis* Erdman and Δesat6 strains grown in Sauton's medium with or without addition of ETZ (80 µM). RNAP-β subunit served as a control for lysis and as a loading control for CL, MPT-32 served as loading control for CF and as a measure of Sec secretion. The CFP-10 and ESAT-6 antibodies detected the EsxB and EsxA protein respectively from WT *M. tuberculosis* Erdman strain. ETZ treatment inhibits the secretion of ESAT-6 and CFP-10. "−−" denotes no ETZ added, whereas "++" denotes ETZ added in both passages and "−+" denotes ETZ added only in second passage. Data are representative of three biological replicates.

ESAT-6 protein is expressed in a phoP mutant strain but it is not exported from the bacterial cell (25). Therefore, ETZ treatment altered the secretion of Esx-1-exported proteins. Mtb Erdman was grown in rich medium and passaged twice in Sauton's minimal medium to measure Esx-1 export. During growth in Sauton's medium the cells were untreated, treated with ETZ during both passages (WT++, FIG. 4), or only treated with ETZ in the final passage (WT−+, FIG. 4). ETZ did not affect ESAT-6 and CFP-10 expression, but strongly and selectively reduced their secretion, as it did not alter that of Sec-secreted protein, Mpt-32 (FIG. 4). Moreover, transcriptional profiling revealed that espR and the espACD operon were significantly down-regulated (p<0.05, >1.5-fold) in ETZ treated cultures (Table 3). Recently, Cao and colleagues have shown that PhoP directly regulates EspR-dependent expression of espACD (26). EspA and ESAT-6 secretion are mutually dependent and loss of espR and espA expression leads to reduced Esx-1 function, loss of ESAT-6 secretion, and attenuated virulence (23, 30). Therefore, both transcriptional profiling and biochemical approaches support that ETZ inhibits the Esx-1 secretion.

Figure 5:
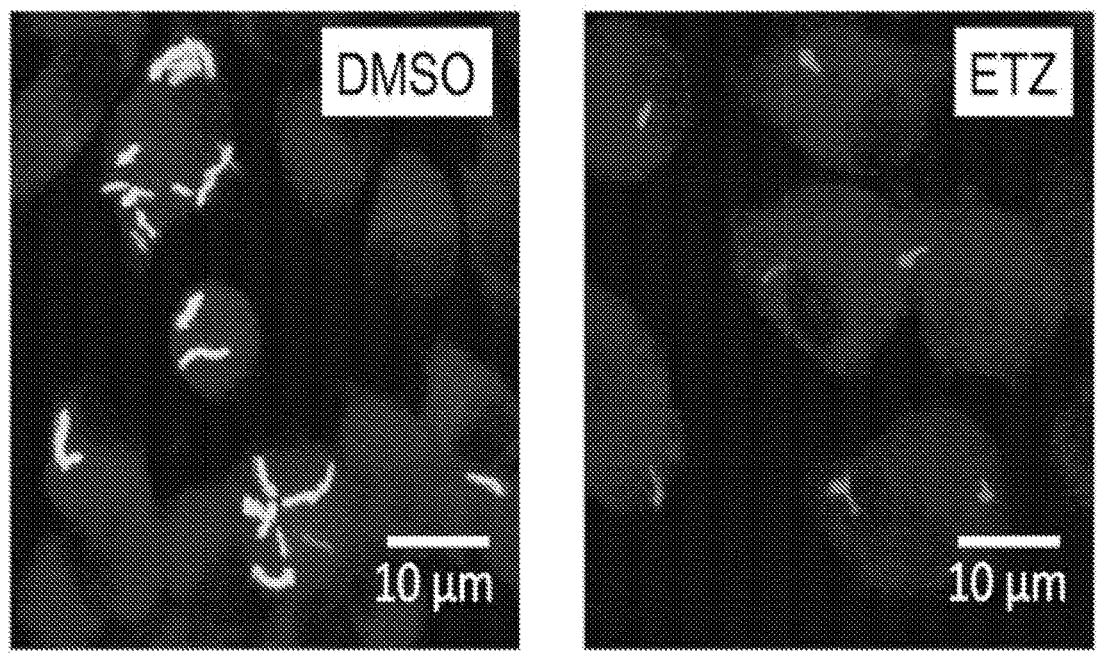
FIG. 5 includes three panels A-C and depicts ETZ modulationg of Mtb gene expression and survival in macrophages. Primary murine BMDM were infected with Mtb CDC1551(aprA'::GFP smyc'::mCherry) PhoPR regulon reporter at an MOI 1:1 and treated with DMSO or ETZ (100 µM) every two days for 9 days. (Panel A) Confocal microscopy images demonstrate that ETZ treatment inhibits the PhoPR regulon in infected macrophages. The merged images show GFP (PhoPR- inducible signal) and mCherry (constitutive signal) fluorescence. (Panel B) Single-cell quantification of reporter fluorescence shows ETZ significantly down-regulates PhoPR-dependent GFP fluorescence compared to a DMSO control. Statistical significance was calculated based on the Mann-Whitney rank test (p<0.001). (Panel C) Treatment of infected BMDMs with 80 µM ETZ reduces growth ~1-log compared to the DMSO control. Data are representative of three biological replicates and statistical significance was calculated based on a two-tailed t-test (p<0.001). Error bars are the standard deviation of three technical replicates.
Figure 5:
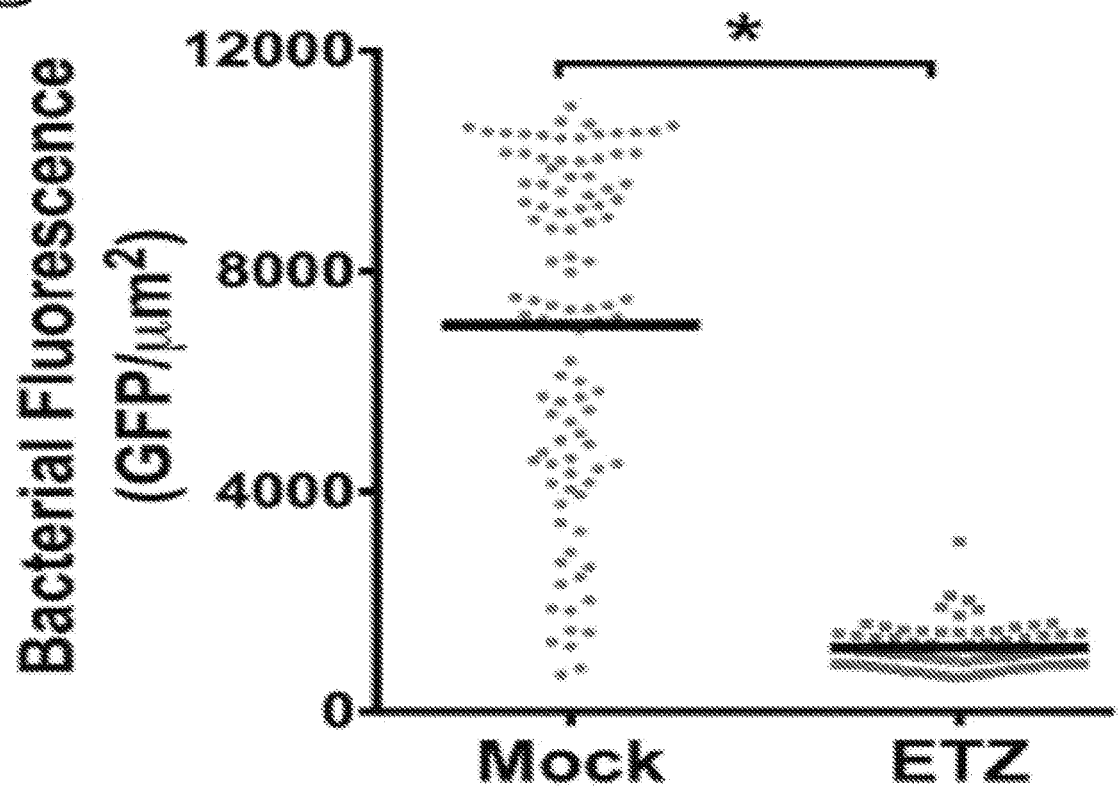
Figure 5:
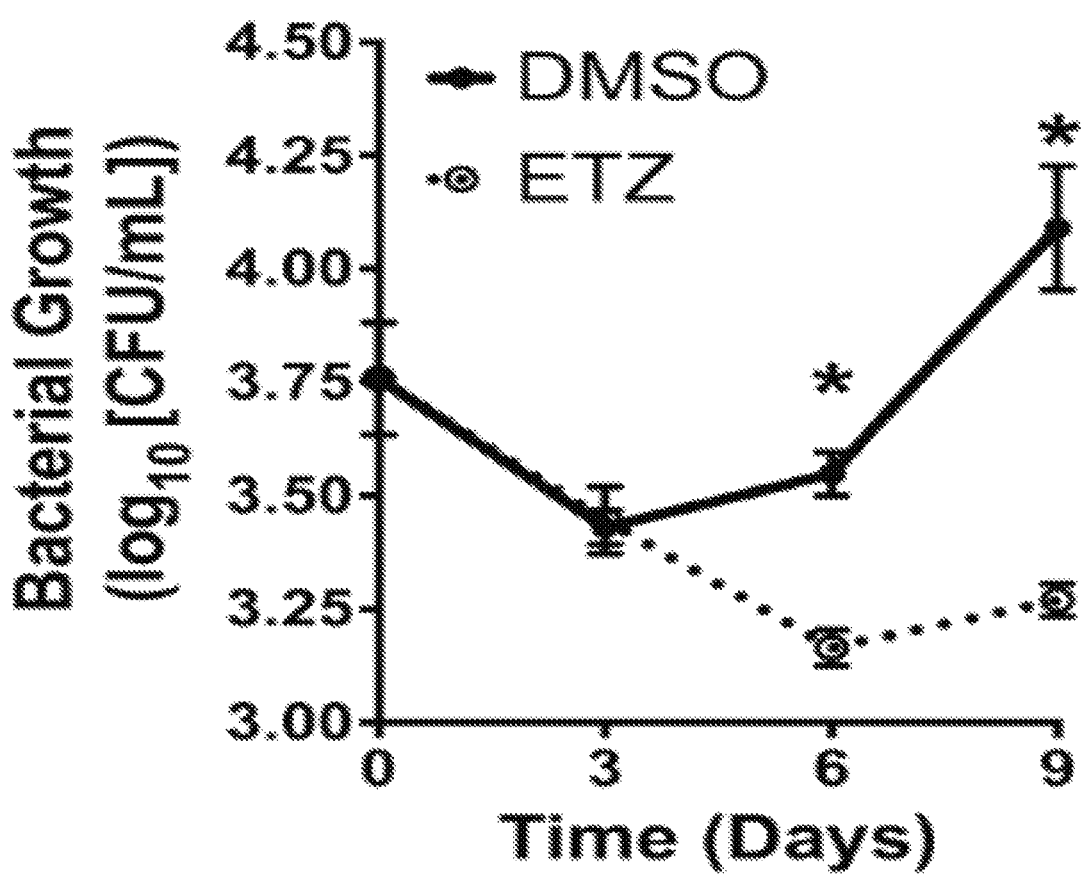

Ethoxzolamide Inhibits Mtb PhoPR Regulon Expression and Growth in Infected Macrophages and Mice The PhoPR regulon is induced within 20 minutes of Mtb phagocytosis by macrophages and remains induced over a period of at least 14 days (32). To determine if ETZ modulates the PhoPR regulon in macrophages, murine bone marrow derived macrophages (BMDMs) were infected with the CDC1551 (aprA'::GFP, smyc'::mCherry) reporter strain. This strain exhibits PhoPR-inducible expression of GFP and constitutive expression of mCherry (5). The infected macrophages were treated with ETZ or DMSO and single-cell reporter fluorescence was quantified 6 days post-infection. ETZ treatment caused >90% inhibition of reporter GFP fluorescence in infected macrophages (FIG. 5, Panel A and B). Moreover, in a 9-day macrophage survival assay, ETZ treatment significantly inhibited the ability of Mtb to grow intracellularly (FIG. 5, Panel C). Notably, both ETZ treated and untreated bacteria exhibited a similar initial decrease in growth during the first 3 days of infection. However, the untreated Mtb successfully adapted to the macrophage environment and grew ~0.5 logs over the next six days while the ETZ treated cells could not transition into a growth phase. This phenotype is similar to that observed with a PhoPR mutant strain (6) and consistent with ETZ functioning as an anti-virulence agent targeting PhoPR-dependent macrophage adaptation.

ETZ is also a eukaryotic CA inhibitor. Therefore, it is possible that the observed intracellular Mtb phenotypes may, in part, be driven by ETZ targeting macrophage CA activity. Because PhoPR is induced by acidic pH in macrophages, whether ETZ inhibits phagosome acidification was also examined. BMDMs were treated with DMSO, ETZ or concanamycin A (an inhibitor of the vacuolar ATPase) four hours prior to being fed with beads coated with the pH-sensitive dye pHrodo. Phagosome acidification was monitored for one hundred minutes using a plate reader. Even at concentrations as high as 100 μM, ETZ did not alter phagosome acidification (FIG. 8, Panel C), supporting the idea that ETZ-induced inhibition of Mtb growth is mediated by PhoPR regulon inhibition, rather than by altering the environment within the macrophage phagosome.

Figure 6:
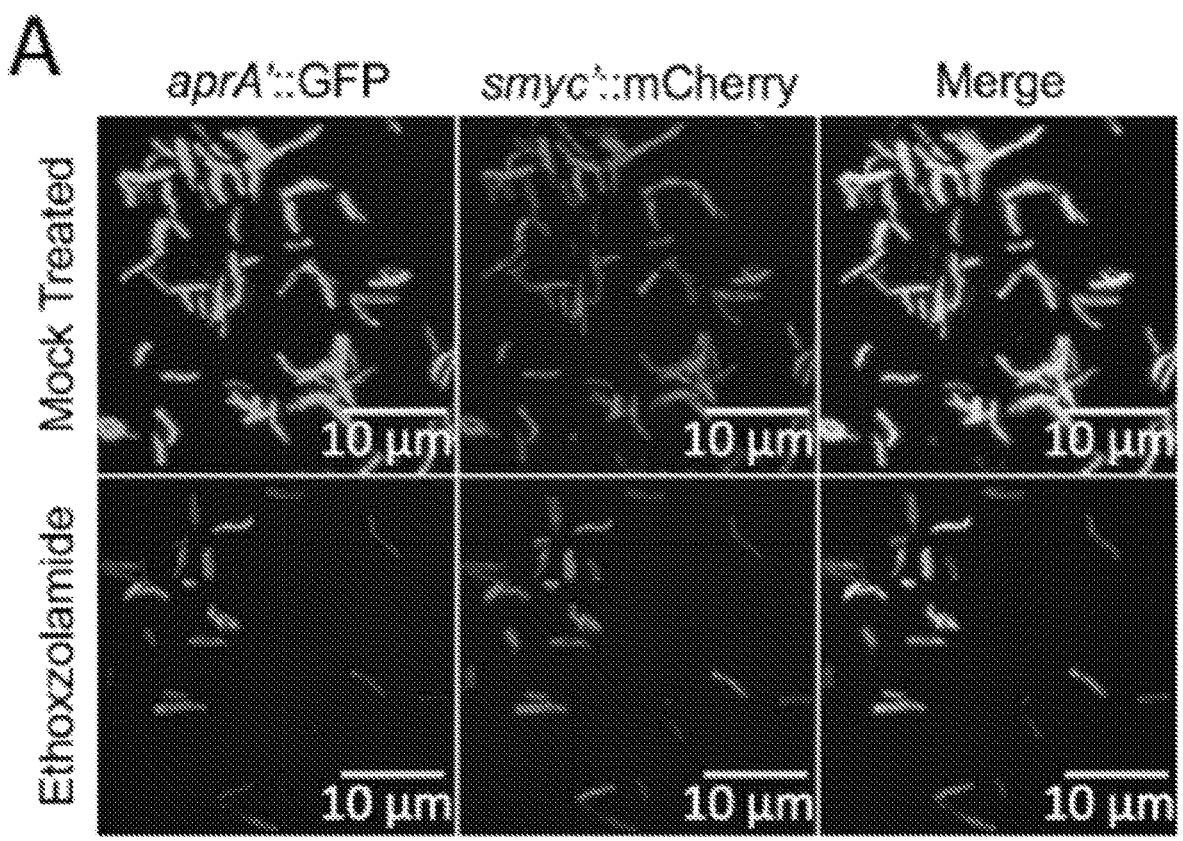
FIG. 6 includes three panels, A-C, and depicts ETZ modulation of PhoPR-regulated gene expression and Mtb survival in vivo. C57Bl/6 mice were infected with 1000 CFU of the Mtb Erdman (aprA'::GFP smyc'::mCherry) fluorescent reporter strain and treated with 100 mg/kg of ETZ for 4 weeks. (Panel A) ETZ down-regulates PhoPR-dependent GFP fluorescence in vivo. Images show reporter fluorescence in mouse lung tissue. (Panel B) Single-cell quantification of reporter fluorescence in infected mouse lungs shows ETZ significantly down-regulates PhoPR-dependent GFP fluorescence as compared to mock treated mice. GFP fluorescence was quantified for ~3000 bacteria. Statistical significance was calculated based on the Mann-Whitney rank test (p<0.0001). (Panel C) Mtb survival is attenuated in ETZ treated lungs. Data presented are from seven animals per treatment group and statistical significance was calculated using a two-tailed t-test (p<0.01). Data are combined from two biological replicates.
Figure 6:
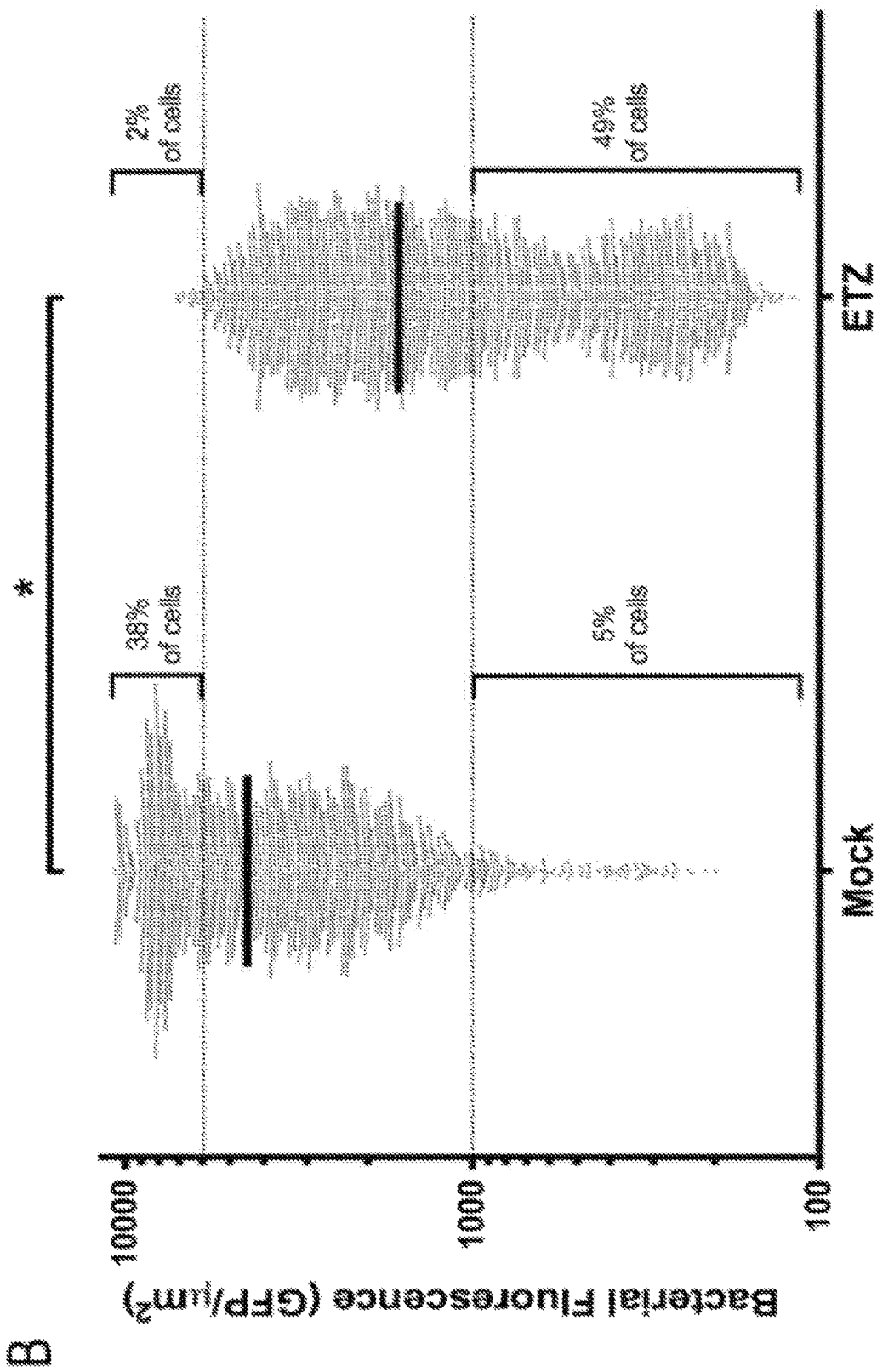
Figure 6:
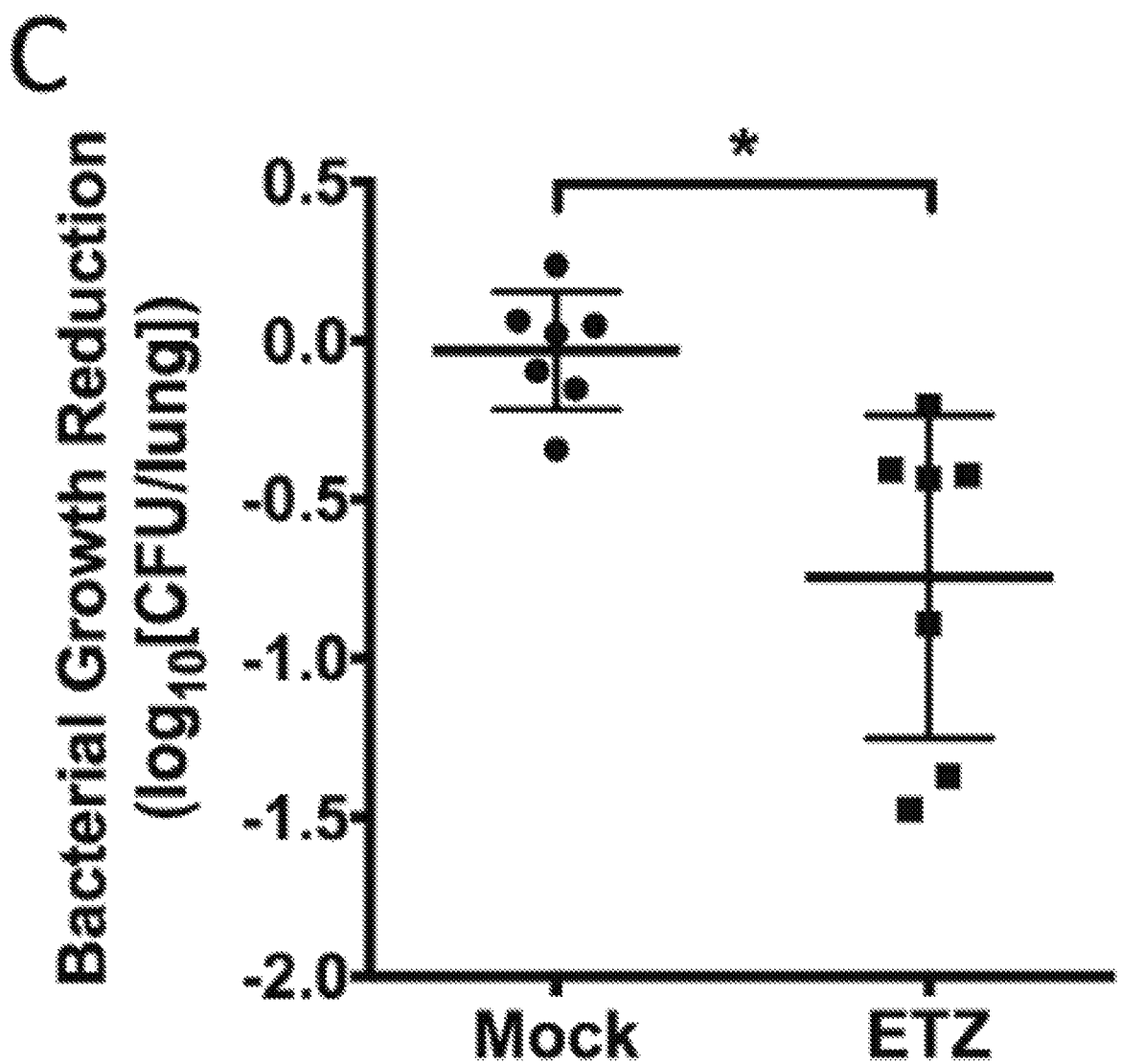
Figure 7:
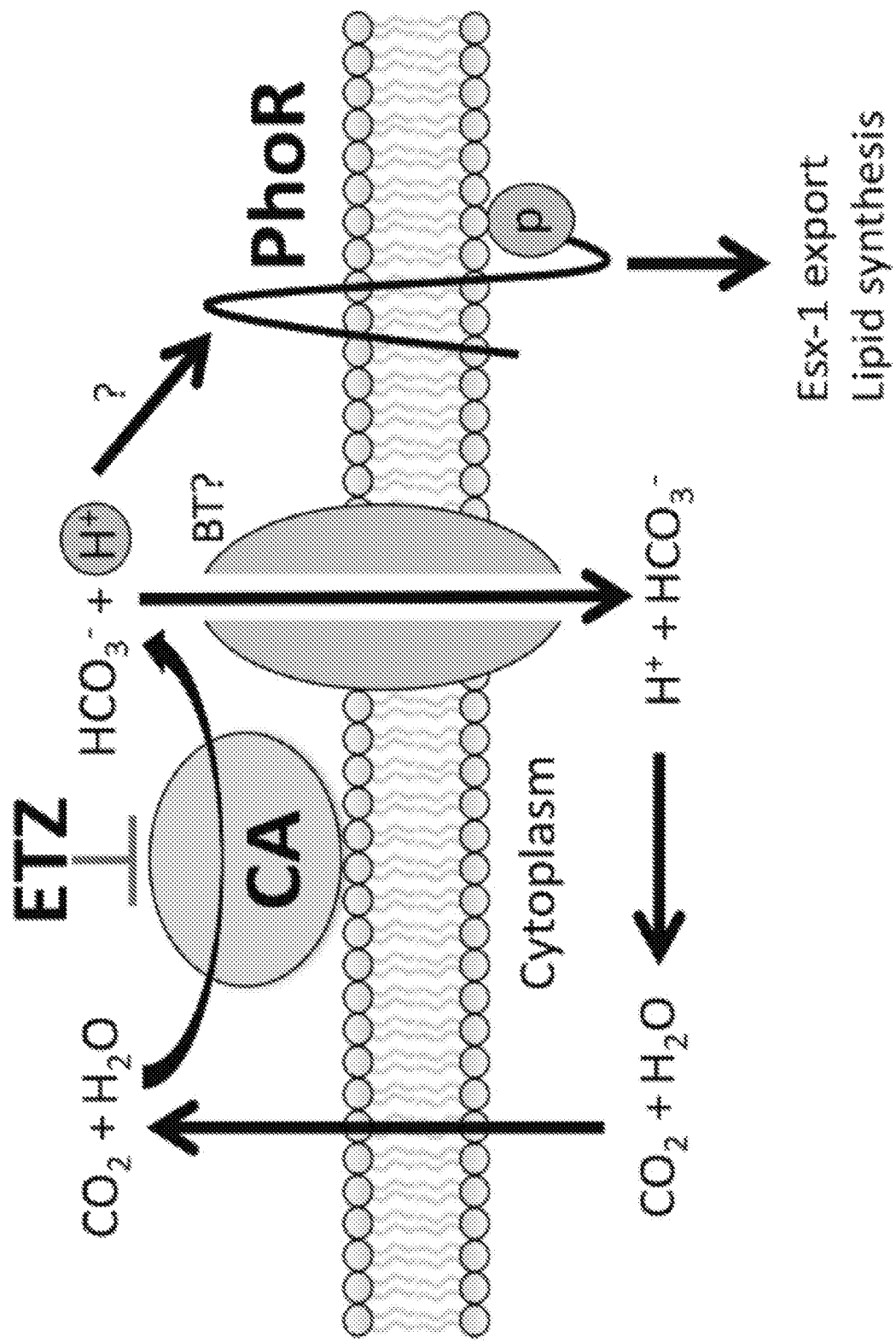
FIG. 7 depicts a model linking ETZ, CA and stimulation of the PhoPR pathway. PhoPR is activated at a similar pH (~6.3) as the dissolved inorganic carbon equilibrium favors CO2 to dissolve in water. CA will interconvert $CO_2+H_2O$ to $HCO_3^-+H^+$. Bicarbonate may be shuttled into the cytoplasm by a bicarbonate transporter (BT) to act in maintaining pH homeostasis or metabolism, while the proton produced in the reaction may promote the acidification of the extracellular environment surrounding PhoR, leading to induction of the PhoPR regulon. ETZ would inhibit this process by inhibiting CA and reducing the accumulation of protons in the pseudoperiplasm.

Next experiments were performed to examiner whether ETZ can modulate the PhoPR regulon in vivo. C57Bl/6 mice were infected with the Erdman (aprA'::GFP smyc'::mCherry) dual fluorescent reporter strain and the mice were treated orally with either 100 mg/kg of ETZ or an equal volume of 0.25% carboxymethyl cellulose (as a mock treatment) 5 days per week for 4 weeks. In animals, ETZ is previously reported to have a short half-life (2.5-5.5 hours) and an $LD_{50}$ of ~1000 mg/kg with no observable drug-related organ lesions observed at 100 mg/kg (33-35). Quantitative single-cell imaging was used to measure the induction of reporter fluorescence in lung tissues. For this approach, lung tissue was sectioned, imaged by confocal microscopy and bacterial fluorescence quantified using Volocity image analysis software (14, 36). Individual bacterial cells were identified using the constitutive mCherry signal and then GFP fluorescence was measured for ~3000 bacterial cells across multiple fields of view from lungs of mice in the same treatment group. Two independent experiments were conducted with similar results; therefore, the data from both experiments were combined for analysis. The Erdman (aprA'::GFP smyc'::mCherry) reporter exhibited a strong induction of GFP fluorescence in infected mice in mock-treated mouse lungs (FIG. 6A). Notably, single cells in the mock treated samples exhibited substantial heterogeneity of GFP fluorescence providing additional evidence that Mtb experiences a variety of microenvironments during the course of infection (FIG. 6, Panel B). In contrast, ETZ strongly down-regulated GFP reporter fluorescence in mouse lungs with 3-fold inhibition of GFP signal as compared to the mock treated control (FIG. 6, Panel B). Importantly, the distribution of reporter fluorescence was dramatically altered by ETZ treatment, with a more homogeneous population of cells expressing low levels of GFP. For example, 49% of Mtb cells in ETZ treated lungs quantified for GFP fluorescence are in the bottom decile of fluorescence (<1000 GFP/m$^2$) as compared to 5% of cells in the mock-treated mice (FIG. 6, Panel B). This approach demonstrates that quantitative analysis of fluorescent Mtb reporter strains in host tissues can be applied as a biomarker for pathway-specific drug exposure in vivo. The effect of ETZ treatment on bacterial survival in vivo was also examined. A significant 0.72 log reduction of bacterial survival in the lungs of ETZ treated mice as compared to the mock-treated control was observed (FIG. 6, Panel C). Therefore, adequate ETZ exposure was achieved in mouse lungs to repress the PhoPR regulon and attenuate virulence. Together, these data support that ETZ functions by an anti-virulence mechanism and attenuates Mtb virulence in vivo by i) targeting Mtb inside macrophages and the mouse lung, ii) downregulating the PhoPR regulon, and iii) reducing the expression of virulence pathways such as lipid metabolism and Esx-1 secretion.

REFERENCES

1. Vandal O H, Nathan C F, Ehrt S. 2009. Acid Resistance in *Mycobacterium tuberculosis*. J Bacteriol 191:4714-4721.
2. Rohde K H, Abramovitch R B, Russell D G. 2007. *Mycobacterium tuberculosis* invasion of macrophages: linking bacterial gene expression to environmental cues. Cell Host Microbe 2:352-364.
3. Walters S B, Dubnau E, Kolesnikova I, Laval F, Daffe M, Smith I. 2006. The *Mycobacterium tuberculosis* PhoPR two-component system regulates genes essential for virulence and complex lipid biosynthesis. Mol Microbiol 60:312-330.
4. Gonzalo-Asensio J, Mostowy S, Harders-Westerveen J, Huygen K, Hernandez-Pando R, Thole J, Behr M, Gicquel B, Martin C. 2008. PhoP: A Missing Piece in the Intricate Puzzle of *Mycobacterium tuberculosis* Virulence. Plos One 3:e3496.
5. Abramovitch R B, Rohde K H, Hsu F F, Russell D G. 2011. aprABC: a *Mycobacterium tuberculosis* complex-specific locus that modulates pH-driven adaptation to the macrophage phagosome. Mol Microbiol 80:678-694.
6. Perez E, Samper S, Bordas Y, Guilhot C, Gicquel B, Martin C. 2001. An essential role for phoP in *Mycobacterium tuberculosis* virulence. Mol Microbiol 41:179-187.
7. Martin C, Williams A, Hernandez-Pando R, Cardona P J, Gormley E, Bordat Y, Soto C Y, Clark S O, Hatch G J, Aguilar D, Ausina V, Gicquel B. 2006. The live *Mycobacterium tuberculosis* phoP mutant strain is more attenuated than BCG and confers protective immunity against tuberculosis in mice and guinea pigs. Vaccine 24:3408-3419.
8. Rasko D A, Sperandio V. 2010. Anti-virulence strategies to combat bacteria-mediated disease. Nature reviews. Drug discovery 9:117-128.
9. Ng W L, Perez L, Cong J, Semmelhack M F, Bassler B L. 2012. Broad spectrum pro-quorum-sensing molecules as inhibitors of virulence in vibrios. PLoS Pathog 8:e1002767.
10. Rasko D A, Moreira C G, Li de R, Reading N C, Ritchie J M, Waldor M K, Williams N, Taussig R, Wei S, Roth M, Hughes D T, Huntley J F, Fina M W, Falck J R, Sperandio V. 2008. Targeting QseC signaling and virulence for antibiotic development. Science 321:1078-1080.
11. Anthouard R, DiRita V J. 2013. Small-molecule inhibitors of toxT expression in *Vibrio cholerae*. mBio 4.
12. Hung D T, Shakhnovich E A, Pierson E, Mekalanos J J. 2005. Small-molecule inhibitor of *Vibrio cholerae* virulence and intestinal colonization. Science 310:670-674.
13. Karginov V A, Nestorovich E M, Moayeri M, Leppla S H, Bezrukov S M. 2005. Blocking anthrax lethal toxin at the protective antigen channel by using structure-inspired drug design. Proc Natl Acad Sci USA 102:15075-15080.
14. Tan S, Sukumar N, Abramovitch R B, Parish T, Russell D G. 2013. *Mycobacterium tuberculosis* Responds to Chloride and pH as Synergistic Cues to the Immune Status of its Host Cell. PLoS Pathog 9:e1003282.
15. Baker J J, Johnson B K, Abramovitch R B. 2014. Slow growth of *Mycobacterium tuberculosis* at acidic pH is regulated by phoPR and host-associated carbon sources. Mol Microbiol 94:56-69.
16. Johnson B K, Abramovitch R B. 2015. Macrophage Infection Models for *Mycobacterium tuberculosis*. Methods Mol Biol 1285:329-341.
17. Brion L P, Schwartz J H, Zavilowitz B J, Schwartz G J. 1988. Micro-method for the measurement of carbonic anhydrase activity in cellular homogenates. Analytical biochemistry 175:289-297.
18. Purdy G E, Niederweis M, Russell D G. 2009. Decreased outer membrane permeability protects mycobacteria from killing by ubiquitin-derived peptides. Mol Microbiol 73:844-857.
19. Schneider C A, Rasband W S, Eliceiri K W. 2012. NIH Image to ImageJ: 25 years of image analysis. Nature methods 9:671-675.
20. Stanley S A, Raghavan S, Hwang W W, Cox J S. 2003. Acute infection and macrophage subversion by *Mycobacterium tuberculosis* require a specialized secretion system. Proc Natl Acad Sci USA 100:13001-13006.
21. Mba Medie F, Champion M M, Williams E A, Champion P A. 2014. Homeostasis of N-alpha-terminal acetylation of EsxA correlates with virulence in *Mycobacterium marinum*. Infect Immun 82:4572-4586.
22. Carta F, Maresca A, Covarrubias A S, Mowbray S L, Jones T A, Supuran C T. 2009. Carbonic anhydrase inhibitors. Characterization and inhibition studies of the most active beta-carbonic anhydrase from *Mycobacterium tuberculosis*, Rv3588c. Bioorg Med Chem Lett 19:6649-6654.
23. Raghavan S, Manzanillo P, Chan K, Dovey C, Cox J S. 2008. Secreted transcription factor controls *Mycobacterium tuberculosis* virulence. Nature 454:717-721.
24. Solans L, Gonzalo-Asensio J, Sala C, Benjak A, Uplekar S, Rougemont J, Guilhot C, Malaga W, Martin C, Cole S T. 2014. The PhoP-dependent ncRNA Mcr7 modulates the TAT secretion system in *Mycobacterium tuberculosis*. PLoS Pathog 10:e1004183.
25. Frigui W, Bottai D, Majlessi L, Monot M, Josselin E, Brodin P, Garnier T, Gicquel B, Martin C, Leclerc C, Cole S T, Brosch R. 2008. Control of *M. tuberculosis* ESAT-6 secretion and specific T cell recognition by PhoP. PLoS Pathog 4:e33.
26. Cao G, Howard S T, Zhang P, Wang X, Chen X L, Samten B, Pang X. 2014. EspR, a regulator of the ESX-1 secretion system in *Mycobacterium tuberculosis*, is directly regulated by the two-component systems MprAB and PhoPR. Microbiology.
27. Sirakova T D, Thirumala A K, Dubey V S, Sprecher H, Kolattukudy P E. 2001. The *Mycobacterium tuberculosis* pks2 gene encodes the synthase for the hepta- and octamethyl-branched fatty acids required for sulfolipid synthesis. J Biol Chem 276:16833-16839.
28. Asensio J G, Maia C, Ferrer N L, Baritone N, Laval F, Soto C Y, Winter N, Daffe M, Gicquel B, Martin C, Jackson M. 2006. The virulence-associated two component PhoP-PhoR system controls the biosynthesis of polyketide-derived lipids in *Mycobacterium tuberculosis*. J Biol Chem 281:1313-1316.
29. Jain M, Petzold C J, Schelle M W, Leavell M D, Mougous J D, Bertozzi C R, Leary J A, Cox J S. 2007. Lipidomics reveals control of *Mycobacterium tuberculosis* virulence lipids via metabolic coupling. Proc Natl Acad Sci USA 104:5133-5138.
30. Fortune S M, Jaeger A, Sarracino D A, Chase M R, Sassetti C M, Sherman D R, Bloom B R, Rubin E J. 2005. Mutually dependent secretion of proteins required for mycobacterial virulence. Proc Natl Acad Sci USA 102: 10676-10681.
31. Rybniker J, Chen J M, Sala C, Hartkoorn R C, Vocat A, Benjak A, Boy-Rottger S, Zhang M, Szekely R, Greff Z, Orfi L, Szabadkai I, Pato J, Keri G, Cole S T. 2014. Anticytolytic Screen Identifies Inhibitors of Mycobacterial Virulence Protein Secretion. Cell Host & Microbe 16:538-548.
32. Rohde K H, Veiga D F, Caldwell S, Balazsi G, Russell D G. 2012. Linking the transcriptional profiles and the physiological states of *Mycobacterium tuberculosis* during an extended intracellular infection. PLoS Pathog 8:e1002769.
33. Drance S M. 1960. Ethoxzolamide (cardrase) in the management of chronic simple glaucoma. Archives of ophthalmology 64:433-437.
34. Drance S M. 1959. The effects of ethoxzolamide (cardrase) on intraocular pressure. Archives of ophthalmology 62:679-684.
35. Moyer J H, Ford R V. 1958. Laboratory and clinical observations on ethoxzolamide (cardrase) as a diuretic agent. The American journal of cardiology 1:497-504.
36. Sukumar N, Tan S, Aldridge B B, Russell D G. 2014. Exploitation of *Mycobacterium tuberculosis* reporter strains to probe the impact of vaccination at sites of infection. PLoS Pathog 10: el004394.
37. Darby C M, Ingolfsson H I, Jiang X, Shen C, Sun M, Zhao N, Burns K, Liu G, Ehrt S, Warren J D, Anderson O S, Brickner S J, Nathan C. 2013. Whole cell screen for inhibitors of pH homeostasis in *Mycobacterium tuberculosis*. PLoS One 8:e68942.
38. Zhao N, Darby C M, Small J, Bachovchin D A, Jiang X, Burns-Huang K E, Botella H, Ehrt S, Boger D L, Anderson E D, Cravatt B F, Speers A E, Fernandez-Vega V, Hodder P S, Eberhart C, Rosen H, Spicer T P, Nathan C F. 2014. Target-Based Screen Against a Periplasmic Serine Protease That Regulates Intrabacterial pH Homeostasis in *Mycobacterium tuberculosis*. ACS chemical biology.
39. de Carvalho L P, Darby C M, Rhee K Y, Nathan C. 2011. Nitazoxanide Disrupts Membrane Potential and Intrabacterial pH Homeostasis of *Mycobacterium tuberculosis*. ACS medicinal chemistry letters 2:849-854.
40. Supuran C T. 2008. Carbonic anhydrases: novel therapeutic applications for inhibitors and activators. Nature reviews. Drug discovery 7:168-181.
41. Arbues A, Aguilo J I, Gonzalo-Asensio J, Marinova D, Uranga S, Puentes E, Fernandez C, Parra A, Cardona P J, Vilaplana C, Ausina V, Williams A, Clark S, Malaga W, Guilhot C, Gicquel B, Martin C. 2013. Construction, characterization and preclinical evaluation of MTBVAC, the first live-attenuated *M. tuberculosis*-based vaccine to enter clinical trials. Vaccine 31:4867-4873.
42. Singh A, Crossman D K, Mai D, Guidry L, Voskuil M I, Renfrow M B, Steyn A J C. 2009. *Mycobacterium tuberculosis* WhiB3 Maintains Redox Homeostasis by Regulating Virulence Lipid Anabolism to Modulate Macrophage Response. Plos Pathog 5:e1000545.
43. Rengarajan J, Bloom B R, Rubin E J. 2005. Genome-wide requirements for *Mycobacterium tuberculosis* adaptation and survival in macrophages. Proc Natl Acad Sci USA 102:8327-8332.
44. Supuran C T. 2011. Bacterial carbonic anhydrases as drug targets: toward novel antibiotics? Frontiers in pharmacology 2:34.
45. Tresguerres M, Buck J, Levin L R. 2010. Physiological carbon dioxide, bicarbonate, and pH sensing. Pflugers Archiv: European journal of physiology 460:953-964.
46. de Souza G A, Leversen N A, Malen H, Wiker H G. 2011. Bacterial proteins with cleaved or uncleaved signal peptides of the general secretory pathway. Journal of proteomics 75:502-510.
47. Slonczewski J L, Fujisawa M, Dopson M, Krulwich T A. 2009. Cytoplasmic pH measurement and homeostasis in bacteria and archaea. Adv Microb Physiol 55:1-79, 317.
48. Sachs G, Weeks D L, Wen Y, Marcus E A, Scott D R, Melchers K. 2005. Acid acclimation by *Helicobacter pylori*. Physiology 20:429-438.
49. Marcus E A, Moshfegh A P, Sachs G, Scott D R. 2005. The periplasmic alpha-carbonic anhydrase activity of *Helicobacter pylori* is essential for acid acclimation. J Bacteriol 187:729-738.
50. Brett D J, Demetriadou C, Zahrt T C. 2011. Adaptation to environmental stimuli within the host: two-component signal transduction systems of *Mycobacterium tuberculosis*. Microbiology and molecular biology reviews: MMBR 75:566-582.
51. Sedlakova O, Svastova E, Takacova M, Kopacek J, Pastorek J, Pastorekova S. 2014. Carbonic anhydrase IX, a hypoxia-induced catalytic component of the pH regulating machinery in tumors. Frontiers in physiology 4:400.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

What is claimed is:

1. A method for treating a subject who is infected with bacterial cells in which the PhoPR regulon is conserved, the method comprising administering to the subject an effective amount of an inhibitor of the PhoPR regulon to thereby treat the infection, wherein the inhibitor of the PhoPR regulon is ethoxzolamide.

2. A method for ameliorating the signs or symptoms of an infection of a subject by bacterial cells in which the PhoPR regulon is conserved, the method comprising administering to the subject an effective amount of an inhibitor of the PhoPR regulon to thereby ameliorate the signs and symptoms of the infection, wherein the inhibitor of the PhoPR regulon is ethoxzolamide.

3. The method according to claim 1, further comprising identifying the subject as having an infection with bacterial cells in which the PhoPR regulon is conserved.

4. The method according to claim 1, wherein the bacteria or bacterial cells are selected from the group consisting of *Mycobacterium, Mycobacterium tuberculosis*, multi-drug resistant *Mycobacterium tuberculosis*, extensively drug resistant *Mycobacterium tuberculosis*, nontuberculosis mycobacterium (NTM), *Clostridium, Bacillus, C. acetobutylicum, B. subtilis, Echerichia coli, Vibrio cholera, Streptomyces coelicolor*, and Enterobacteriaceae.

5. The method according to claim 1, wherein the inhibitor is orally administered, parenterally administered, intravenously administered, administered as an aerosol, administered using a nebulizer or inhaler, topically administered, administered as an eye drop, administered as a cream, an ointment, or a lotion, or present on a bandage or dressing applied to an infected site to the subject.

6. The method according to claim 1, wherein the subject has a lung infection, skin infection, or eye infection.

7. A method according to claim 1, wherein the subject is afflicted with tuberculosis, multi-resistant tuberculosis, or extensively multidrug resistant tuberculosis.

8. The method according to claim 1, wherein the subject is a human.

9. The method according to claim 1 for eliminating dormant *Mycobacterium tuberculosis* cells in a subject afflicted with latent tuberculosis, the method comprising administering to the subject an effective amount of ethoxzolamide to thereby eliminate dormant *Mycobacterium tuberculosis* cells in the subject and treat latent tuberculosis.

10. The method according to claim 1, wherein the effective amount of ethoxzolamide is between 0.01 and 100 mg/kg body weight of the subject.

11. The method according to claim 1, wherein the ethoxzolamide is administered in combination with one or more antibiotics selected from the group consisting of isoniazid, rifampicin, ethambutol, and pyrazinamide.

12. The method according to claim 1, wherein the ethoxzolamide is administered for less than 6 weeks or between 2 to 4 weeks.

13. The method according to claim 2, further comprising identifying the subject as having an infection with bacterial cells in which the PhoPR regulon is conserved.

14. The method according to claim 2, wherein the bacteria or bacterial cells are selected from the group consisting of *Mycobacterium, Mycobacterium tuberculosis*, multi-drug resistant *Mycobacterium tuberculosis*, extensively drug resistant *Mycobacterium tuberculosis*, nontuberculosis mycobacterium (NTM), *Clostridium, Bacillus, C. acetobutylicum, B. subtilis, Echerichia coli, Vibrio cholera, Streptomyces coelicolor*, and Enterobacteriaceae.

15. The method according to claim 2, wherein the inhibitor is orally administered, parenterally administered, intravenously administered, administered as an aerosol, administered using a nebulizer or inhaler, topically administered, administered as an eye drop, administered as a cream, an ointment, or a lotion, or present on a bandage or dressing applied to an infected site to the subject.

16. The method according to claim 2, wherein the subject has a lung infection, skin infection, or eye infection.

17. A method according to claim 2, wherein the subject is afflicted with tuberculosis, multi-resistant tuberculosis, or extensively multidrug resistant tuberculosis.

18. The method according to claim 2, wherein the subject is a human.

19. The method according to claim 2, for eliminating dormant *Mycobacterium tuberculosis* cells in a subject afflicted with latent tuberculosis, the method comprising administering to the subject an effective amount of ethoxzolamide to thereby eliminate dormant *Mycobacterium tuberculosis* cells in the subject and treat latent tuberculosis.

20. The method according to claim 2, wherein the effective amount of ethoxzolamide is between 0.01 and 100 mg/kg body weight of the subject.

21. The method according to claim 2, wherein the ethoxzolamide is administered in combination with one or more antibiotics selected from the group consisting of isoniazid, rifampicin, ethambutol, and pyrazinamide.

22. The method according to claim 2, wherein the ethoxzolamide is administered for less than 6 weeks or between 2 to 4 weeks.

\* \* \* \* \*

SEQUENCE LISTING

<160> NUMBER OF SEQ ID NOS: 3

<210> SEQ ID NO 1
<211> LENGTH: 764
<212> TYPE: PRT
<213> ORGANISM: Mycobacterium tuberculosis

<400> SEQUENCE: 1

```
Met Thr Ile Pro Arg Ser Gln His Met Ser Thr Ala Val Asn Ser Cys
 1               5                  10                  15

Thr Glu Ala Pro Ala Ser Arg Ser Gln Trp Met Leu Ala Asn Leu Arg
             20                  25                  30

His Asp Val Pro Ala Ser Leu Val Phe Leu Val Ala Leu Pro Leu
         35                  40                  45

Ser Leu Gly Ile Ala Ile Ala Ser Gly Ala Pro Ile Ile Ala Gly Val
     50                  55                  60

Ile Ala Ala Val Val Gly Gly Ile Val Ala Gly Ala Val Gly Gly Ser
 65                  70                  75                  80

Pro Val Gln Val Ser Gly Pro Ala Ala Gly Leu Thr Val Val Ala
                 85                  90                  95

Glu Leu Ile Asp Glu Leu Gly Trp Pro Met Leu Cys Leu Met Thr Ile
                100                 105                 110

Ala Ala Gly Ala Leu Gln Ile Val Phe Gly Leu Ser Arg Met Ala Arg
            115                 120                 125

Ala Ala Leu Ala Ile Ala Pro Val Val His Ala Met Leu Ala Gly
            130                 135                 140

Ile Gly Ile Thr Ile Ala Leu Gln Gln Ile His Val Leu Leu Gly Gly
145                 150                 155                 160

Thr Ser His Ser Ser Ala Trp Arg Asn Ile Val Ala Leu Pro Asp Gly
                165                 170                 175

Ile Leu His His Glu Leu His Glu Val Ile Val Gly Gly Thr Val Ile
            180                 185                 190

Ala Ile Leu Leu Met Trp Ser Lys Leu Pro Ala Lys Val Arg Ile Ile
            195                 200                 205

Pro Gly Pro Leu Val Ala Ile Ala Gly Ala Thr Val Leu Ala Leu Leu
        210                 215                 220

Pro Val Leu Gln Thr Glu Arg Ile Asp Leu Gln Gly Asn Phe Phe Asp
225                 230                 235                 240

Ala Ile Gly Leu Pro Lys Leu Ala Glu Met Ser Pro Gly Gly Gln Pro
                245                 250                 255

Trp Ser His Glu Ile Ser Ala Ile Ala Leu Gly Val Leu Thr Ile Ala
            260                 265                 270

Leu Ile Ala Ser Val Glu Ser Leu Leu Ser Ala Val Gly Val Asp Lys
        275                 280                 285

Leu His His Gly Pro Arg Thr Asp Phe Asn Arg Glu Met Val Gly Gln
        290                 295                 300

Gly Ser Ala Asn Val Val Ser Gly Leu Leu Gly Gly Leu Pro Ile Thr
305                 310                 315                 320

Gly Val Ile Val Arg Ser Ser Ala Asn Val Ala Ala Gly Ala Arg Thr
                325                 330                 335

Arg Met Ser Thr Ile Leu His Gly Val Trp Ile Leu Leu Phe Ala Ser
            340                 345                 350

Leu Phe Thr Asn Leu Val Glu Leu Ile Pro Lys Ala Ala Leu Ala Gly
        355                 360                 365
```

-continued

Leu Leu Ile Val Ile Gly Ala Gln Leu Val Lys Leu Ala His Ile Lys
         370                 375                 380

Leu Ala Trp Arg Thr Gly Asn Phe Val Ile Tyr Ala Ile Thr Ile Val
385                 390                 395                 400

Cys Val Val Phe Leu Asn Leu Leu Glu Gly Val Ala Ile Gly Leu Val
                405                 410                 415

Val Ala Ile Val Phe Leu Leu Val Arg Val Arg Ala Pro Val Glu
                420                 425                 430

Val Lys Pro Val Gly Gly Glu Gln Ser Lys Arg Trp Arg Val Asp Ile
                435                 440                 445

Asp Gly Thr Leu Ser Phe Leu Leu Leu Pro Arg Leu Thr Thr Val Leu
        450                 455                 460

Ser Lys Leu Pro Glu Gly Ser Glu Val Thr Leu Asn Leu Asn Ala Asp
465                 470                 475                 480

Tyr Ile Asp Asp Ser Val Ser Glu Ala Ile Ser Asp Trp Arg Arg Ala
                485                 490                 495

His Glu Thr Arg Gly Gly Val Val Ala Ile Val Glu Thr Ser Pro Ala
                500                 505                 510

Lys Leu His His Ala His Ala Arg Pro Pro Lys Arg His Phe Ala Ser
        515                 520                 525

Asp Pro Ile Gly Leu Val Pro Trp Arg Ser Ala Arg Gly Lys Asp Arg
        530                 535                 540

Gly Ser Ala Ser Val Leu Asp Arg Ile Asp Glu Tyr His Arg Asn Gly
545                 550                 555                 560

Ala Ala Val Leu His Pro His Ile Ala Gly Leu Thr Asp Ser Gln Asp
                565                 570                 575

Pro Tyr Glu Leu Phe Leu Thr Cys Ala Asp Ser Arg Ile Leu Pro Asn
                580                 585                 590

Val Ile Thr Ala Ser Gly Pro Gly Asp Leu Tyr Thr Val Arg Asn Leu
                595                 600                 605

Gly Asn Leu Val Pro Thr Asp Pro Asp Arg Ser Val Asp Ala Ala
        610                 615                 620

Leu Asp Phe Ala Val Asn Gln Leu Gly Val Ser Ser Val Val Cys
625                 630                 635                 640

Gly His Ser Ser Cys Ala Ala Met Thr Ala Leu Leu Glu Asp Pro
                645                 650                 655

Ala Asn Thr Thr Thr Pro Met Met Arg Trp Leu Glu Asn Ala His Asp
                660                 665                 670

Ser Leu Val Val Phe Arg Asn His His Pro Ala Arg Arg Ser Ala Glu
        675                 680                 685

Ser Ala Gly Tyr Pro Glu Ala Asp Gln Leu Ser Ile Val Asn Val Ala
        690                 695                 700

Val Gln Val Glu Arg Leu Thr Arg His Pro Ile Leu Ala Thr Ala Val
705                 710                 715                 720

Ala Ala Ala Asp Leu Gln Val Ile Gly Ile Phe Phe Asp Ile Ser Thr
                725                 730                 735

Ala Arg Val Tyr Glu Val Gly Pro Asn Gly Ile Ile Cys Pro Asp Glu
                740                 745                 750

Pro Ala Asp Arg Pro Val Asp His Glu Ser Ala Gln
                755                 760

<210> SEQ ID NO 2
<211> LENGTH: 163
<212> TYPE: PRT

<213> ORGANISM: Mycobacterium tuberculosis

<400> SEQUENCE: 2

```
Met Thr Val Thr Asp Asp Tyr Leu Ala Asn Asn Val Asp Tyr Ala Ser
1               5                   10                  15

Gly Phe Lys Gly Pro Leu Pro Met Pro Pro Ser Lys His Ile Ala Ile
            20                  25                  30

Val Ala Cys Met Asp Ala Arg Leu Asp Val Tyr Arg Met Leu Gly Ile
        35                  40                  45

Lys Glu Gly Glu Ala His Val Ile Arg Asn Ala Gly Cys Val Val Thr
    50                  55                  60

Asp Asp Val Ile Arg Ser Leu Ala Ile Ser Gln Arg Leu Leu Gly Thr
65                  70                  75                  80

Arg Glu Ile Ile Leu Leu His His Thr Asp Cys Gly Met Leu Thr Phe
                85                  90                  95

Thr Asp Asp Asp Phe Lys Arg Ala Ile Gln Asp Glu Thr Gly Ile Arg
            100                 105                 110

Pro Thr Trp Ser Pro Glu Ser Tyr Pro Asp Ala Val Glu Asp Val Arg
        115                 120                 125

Gln Ser Leu Arg Arg Ile Glu Val Asn Pro Phe Val Thr Lys His Thr
    130                 135                 140

Ser Leu Arg Gly Phe Val Phe Asp Val Ala Thr Gly Lys Leu Asn Glu
145                 150                 155                 160

Val Thr Pro
```

<210> SEQ ID NO 3
<211> LENGTH: 207
<212> TYPE: PRT
<213> ORGANISM: Mycobacterium tuberculosis

<400> SEQUENCE: 3

```
Met Pro Asn Thr Asn Pro Val Ala Ala Trp Lys Ala Leu Lys Glu Gly
1               5                   10                  15

Asn Glu Arg Phe Val Ala Gly Arg Pro Gln His Pro Ser Gln Ser Val
            20                  25                  30

Asp His Arg Ala Gly Leu Ala Ala Gly Gln Lys Pro Thr Ala Val Ile
        35                  40                  45

Phe Gly Cys Ala Asp Ser Arg Val Ala Ala Glu Ile Ile Phe Asp Gln
    50                  55                  60

Gly Leu Gly Asp Met Phe Val Val Arg Thr Ala Gly His Val Ile Asp
65                  70                  75                  80

Ser Ala Val Leu Gly Ser Ile Glu Tyr Ala Val Thr Val Leu Asn Val
                85                  90                  95

Pro Leu Ile Val Val Leu Gly His Asp Ser Cys Gly Ala Val Asn Ala
            100                 105                 110

Ala Leu Ala Ala Ile Asn Asp Gly Thr Leu Pro Gly Gly Tyr Val Arg
        115                 120                 125

Asp Val Val Glu Arg Val Ala Pro Ser Val Leu Leu Gly Arg Arg Asp
    130                 135                 140

Gly Leu Ser Arg Val Asp Glu Phe Glu Gln Arg His Val His Glu Thr
145                 150                 155                 160

Val Ala Ile Leu Met Ala Arg Ser Ser Ala Ile Ser Glu Arg Ile Ala
                165                 170                 175

Gly Gly Ser Leu Ala Ile Val Gly Val Thr Tyr Gln Leu Asp Asp Gly
            180                 185                 190
```

```
Arg Ala Val Leu Arg Asp His Ile Gly Asn Ile Gly Glu Glu Val
    195                 200                 205
```